(12) United States Patent
Golan

(10) Patent No.: US 12,000,494 B2
(45) Date of Patent: Jun. 4, 2024

(54) SEALING VALVE

(71) Applicant: BREVEL LTD., Rehovot (IL)

(72) Inventor: Ido Golan, Rehovot (IL)

(73) Assignee: BREVEL LTD., Rehovot (IL)

( * ) Notice: Subject to any disclaimer, the term of this patent is extended or adjusted under 35 U.S.C. 154(b) by 6 days.

(21) Appl. No.: 17/792,851

(22) PCT Filed: Mar. 9, 2021

(86) PCT No.: PCT/IL2021/050256
§ 371 (c)(1),
(2) Date: Jul. 14, 2022

(87) PCT Pub. No.: WO2021/181385
PCT Pub. Date: Sep. 16, 2021

(65) Prior Publication Data
US 2023/0052876 A1 Feb. 16, 2023

(30) Foreign Application Priority Data

Mar. 11, 2020 (IL) .......................................... 273241

(51) Int. Cl.
*F16K 15/14* (2006.01)
*F16K 15/18* (2006.01)

(52) U.S. Cl.
CPC ........ *F16K 15/147* (2013.01); *F16K 15/1401* (2021.08); *F16K 15/1825* (2021.08); *Y10T 137/784* (2015.04); *Y10T 137/7842* (2015.04); *Y10T 137/7898* (2015.04)

(58) Field of Classification Search
CPC ............... F16K 15/147; F16K 15/1401; F16K 15/1825; Y10T 137/784; Y10T 137/7842; Y10T 137/7879
See application file for complete search history.

(56) References Cited

U.S. PATENT DOCUMENTS

| 4,038,983 A | * | 8/1977 | Mittleman | ............ A61M 39/24 604/185 |
| 4,054,152 A | * | 10/1977 | Ito | ......................... F16K 15/148 137/854 |
| 4,332,249 A | * | 6/1982 | Joslin | .................... A61M 39/24 604/36 |

(Continued)

FOREIGN PATENT DOCUMENTS

| DE | 3202796 A1 | 8/1983 |
| EP | 0901389 B1 | 9/2004 |

(Continued)

OTHER PUBLICATIONS

PCT International Search Report for International Application No. PCT/IL2021/050256, dated May 3, 2021, 3pp.

(Continued)

*Primary Examiner* — Daphne M Barry
*Assistant Examiner* — Frederick D Soski
(74) *Attorney, Agent, or Firm* — The Roy Gross Law Firm, LLC; Roy Gross

(57) ABSTRACT

The present invention relates to sealing valves that can be mounted within a container wall, enabling controlled fluid flow along both inner and outer surfaces of the sealing valve in the same distal direction.

20 Claims, 30 Drawing Sheets

(56) References Cited

U.S. PATENT DOCUMENTS

| | | | | |
|---|---|---|---|---|
| 5,190,067 A * | 3/1993 | Paradis | ............... | A61M 39/24 604/83 |
| 6,053,896 A | 4/2000 | Wilson et al. | | |
| 9,335,000 B2 | 5/2016 | Selker et al. | | |
| 2006/0253084 A1* | 11/2006 | Nordgren | ............. | F16K 15/147 604/247 |
| 2007/0131725 A1* | 6/2007 | Friedman | ............... | B67D 3/043 222/518 |
| 2008/0185062 A1 | 8/2008 | Johannes Nijland | | |
| 2012/0244019 A1* | 9/2012 | Otsuka | ............... | F16K 15/148 417/295 |
| 2013/0041258 A1 | 2/2013 | Patrick et al. | | |
| 2013/0316034 A1* | 11/2013 | Bauer | .................... | B29C 39/24 29/890.121 |
| 2015/0247504 A1* | 9/2015 | Moormann | ........ | F04D 15/0022 417/36 |
| 2016/0228689 A1* | 8/2016 | Ferguson | ............. | A61J 15/0092 |
| 2016/0270446 A1* | 9/2016 | Shenkal | ................. | H05B 3/40 |
| 2017/0030472 A1* | 2/2017 | Hall | ..................... | F16K 15/147 |
| 2018/0038497 A1* | 2/2018 | Veto | ..................... | F16K 15/148 |
| 2018/0043149 A1* | 2/2018 | Martin | ................. | F16K 15/147 |
| 2019/0138032 A1* | 5/2019 | Shevgoor | ............. | F16K 15/147 |
| 2019/0358667 A1* | 11/2019 | Gaus | .................... | B05C 17/005 |
| 2020/0201362 A1* | 6/2020 | Shevgoor | ............. | G05D 7/0113 |
| 2021/0310579 A1* | 10/2021 | Maleki | ................. | F16K 15/148 |
| 2022/0163135 A1* | 5/2022 | Maleki | ................. | F16K 15/142 |

FOREIGN PATENT DOCUMENTS

| | | |
|---|---|---|
| JP | 2006266414 A | 10/2006 |
| WO | 2020158612 A1 | 8/2020 |

OTHER PUBLICATIONS

PCT Written Opinion for International Application No. PCT/IL2021/050256, dated May 3, 2021, 4pp.

PCT International Preliminary Report on Patentability for International Application No. PCT/IL2021/050256, dated Sep. 6, 2022, 5pp.

Minivalve; Dome valves and cross slit valves with back-up seal, how they work (patent pending). Retrieved from: http://www.minivalve.com/newsite/index.php/en/by-type/cross-slit-valves/how-they-work, on Mar. 25, 2020. 1 page.

Minivalve; Duckbill/Umbrella combination valves, how they work. Retrieved from: http://www.minivalve.com/newsite/index.php/en/by-type/duckbill-umbrella-combination-valves/how-they-work, on Mar. 25, 2020. 2 pages.

\* cited by examiner

SEALING VALVE

CROSS REFERENCE TO RELATED APPLICATIONS

This application is a National Phase of PCT Patent Application No. PCT/IL2021/050256 having International filing date of Mar. 9, 2021, which claims the benefit of Israeli Patent Application No. 273241, filed Mar. 11, 2020, the contents of which are all incorporated herein by reference in their entirety.

FIELD OF THE INVENTION

The present invention relates to sealing valves that can be mounted within a container wall, enabling controlled fluid flow along both inner and outer surfaces of the sealing valve in the same distal direction.

BACKGROUND OF THE INVENTION

Sealing valves are conventionally used for a wide range of applications, providing sealing functionality between an interior cavity of a container that needs to be hermetically sealed, and components that may attach to or protrude into the internal hermetically sealed volume, such as various tubes, catheters, pipes, cables and the like.

In some applications, the interior hermetically sealed cavity of the container needs to be periodically cleaned or sanitized, which may require removal of the components attached to the container to enable flow of cleaning solutions into the internal cavity of the container. Some sealing valves are integrated with valve portions, which allow fluid, such as cleaning solutions, to flow into the internal cavity of the container, in a manner that does not require removal of the seal or the components sealed thereby against the container. However, in many occasions, the sealing valves themselves may give rise to accumulation of debris in pocket-like portions that may be exposed to the external environment, such as internal seal surfaces extending toward tubular structures extending there-through, and may require cleaning or sanitizing of such portions in a manner that may still require removal of the sealing valve. Thus, there is a need to provide sealing valves that will allow fluid flow of cleaning solutions or any other type of fluid, for example during periodic cleaning or sanitization procedures, while the sealing valve and the tubular component sealed thereby remain in position against the wall of the container.

SUMMARY OF THE INVENTION

The present disclosure is directed toward sealing valves for directing fluids along the inner surfaces and the outer surfaces of the sealing valves, in the same distal direction toward an internal cavity of a container. Further disclosed are sealing assemblies, including the sealing valve mounted against a container wall, which may be any wall of the sealed container, such as a container sidewall of a container cover.

According to one aspect of the invention, there is provided a sealing valve comprising a main tubular body, extending longitudinally between a proximal end and a distal end. The main tubular body comprises a proximal segment, extending distally from the proximal end, and a tapering segment, extending from the proximal segment and tapering radially inward in the distal direction.

The sealing valve further comprises a membrane portion extending around and radially away from the main tubular body, and comprising a membrane juncture along which the membrane valve portion is attached to the main tubular body, a membrane body extending radially away from the membrane juncture, and a membrane lip.

The membrane valve portion is resiliently biased toward the proximal direction, and is configured to bend distally when flow-induced pressure gradient is applied thereto by fluid flowing in the distal direction.

The distal end is configured to transition between a distal free state, when no tube extends there-through, and a distal sealed state, when a tube extends there-through, so as to seal against the tube while no flow-induced pressure gradient is applied thereto.

The distal end is made of a resilient flexible material, configured to expand in the radial direction away from the tube extending there-through, when fluid pressure is applied to the distal end by distally-oriented fluid flow through the main tubular body.

According to some embodiments, the sealing valve further comprises a proximal flange extending radially outward from the proximal segment.

According to some embodiments, the sealing valve further comprises a distal segment extending between the tapering segment and the distal end. The distal segment is configured to transition between the distal free state and the distal sealed state, while no flow-induced pressure gradient is applied thereto. The distal segment is made of a resilient flexible material, configured to expand in the radial direction when fluid pressure is applied to the distal end by distally-flowing fluid.

According to some embodiments, the distal segment comprises a plurality of flaps, resiliently biased radially inward.

According to some embodiments, the membrane lip is a rounded membrane lip.

According to some embodiments, the membrane lip is a flat membrane lip.

According to some embodiments, the membrane body is arched from the membrane juncture in the proximal direction.

According to some embodiments, the main tubular body further comprises at least one side opening, proximal to the membrane juncture.

According to some embodiments, the sealing valve further comprises a proximal seal extending radially inward from the proximal segment.

According to some embodiments, the membrane body comprises a proximal flat surface section.

According to some embodiments, the membrane valve portion further comprises a depressed surface section between the proximal flat surface section and the membrane juncture.

According to some embodiments, there is provided a sealing assembly comprising a container wall and the sealing valve. The container wall comprises a proximal wall surface, a distal wall surface, and at least one central bore. The at least one sealing valve is mounted within the at least one central bore, such that the main tubular body extends through the at least one central bore.

According to some embodiments, the container wall is a top cover of a container.

According to some embodiments, the container wall further comprises at least one peripheral opening, offset radially outward from the at least one central bore.

According to some embodiments, the sealing assembly further comprises the tube extending axially through the main tubular body.

According to some embodiments, the distal wall surface comprises a receiving channel, dimensioned to receive and accommodate the membrane lip.

According to some embodiments, the central bore comprises a bore groove, spaced away from both the proximal wall surface and the distal wall surface, and configured to accommodate the proximal flange.

According to some embodiments, the central bore comprises a bore recess, spaced away from the distal wall surface and open ended along the proximal wall surface, wherein the central bore is configured to accommodate the proximal flange.

According to some embodiments, the container wall further comprises at least one hollow extension, extending proximally from the proximal wall surface around the central bore.

According to some embodiments, the sealing assembly further comprises at least one separable cap, configured to threadedly engage with the at least one hollow extension, and at least one gasket situated between the at least one separable cap and the at least one hollow extension.

According to some embodiments, the at least one hollow extension comprises an extension inlet opening.

According to some embodiments, the sealing assembly further comprises a peripheral inlet chamber, comprising at least one peripheral chamber sidewall extending proximally from the proximal wall surface, a peripheral chamber proximal wall extending between the at least one peripheral chamber sidewall and the at least one hollow extension, and a peripheral chamber opening. The at least one peripheral chamber sidewall is disposed radially away from the at least one peripheral opening.

According to some embodiments, the peripheral chamber proximal wall is distal to the extension inlet opening of the at least one hollow extension.

According to some embodiments, the sealing assembly further comprises a central inlet chamber, comprising at least one central chamber sidewall extending proximally from the proximal wall surface or from the peripheral chamber proximal wall, a central chamber proximal wall extending between the at least one central chamber sidewall and the at least one hollow extension, and a central chamber opening. The central chamber proximal wall is proximal to the extension inlet opening of the at least one hollow extension.

According to some embodiments, the central inlet chamber encompasses a plurality of hollow extensions.

According to some embodiments, the peripheral inlet chamber encompasses a plurality of hollow extensions.

Certain embodiments of the present invention may include some, all, or none of the above advantages. Further advantages may be readily apparent to those skilled in the art from the figures, descriptions, and claims included herein. Aspects and embodiments of the invention are further described in the specification herein below and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

The following embodiments and aspects thereof are described and illustrated in conjunction with systems, tools and methods which are meant to be exemplary and illustrative, but not limiting in scope. In various embodiments, one or more of the above-described problems have been reduced or eliminated, while other embodiments are directed to other advantages or improvements.

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention.

For the sake of clarity, some objects depicted in the figures are not to scale.

In the Figures:

FIG. 1A shows a perspective view of a sealing valve in a peripheral free state, according to some implementations.

FIG. 1B shows a sectional view in perspective of the sealing valve of FIG. 1A.

FIG. 2A shows a perspective view of the sealing valve of FIG. 1A in a peripheral open state.

FIG. 2B shows a sectional view in perspective of the sealing valve of FIG. 2A.

FIG. 3 shows a cross-sectional view of a sealing assembly that includes a sealing valve mounted within a container wall, according to some implementations.

FIG. 4 shows a cross-sectional view of the sealing assembly of FIG. 3, having a tube extending through the sealing valve.

FIG. 5A shows a cross-sectional view of the sealing assembly of FIG. 4, in a peripheral sealed state and a distal sealed state of the sealing valve.

FIG. 5B shows a cross-sectional view of the sealing assembly of FIG. 5A, in a peripheral open state and a distal sealed state of the sealing valve.

FIG. 5C shows a cross-sectional view of the sealing assembly of FIG. 5A, in a peripheral sealed state and a distal open state of the sealing valve.

FIG. 6 shows a perspective view of a sealing valve provided with a flat membrane lip, according to some implementations.

FIG. 7 shows a cross-sectional view of the sealing valve of FIG. 6 mounted within a container wall having a bore groove, according to some implementations.

Figure 6:
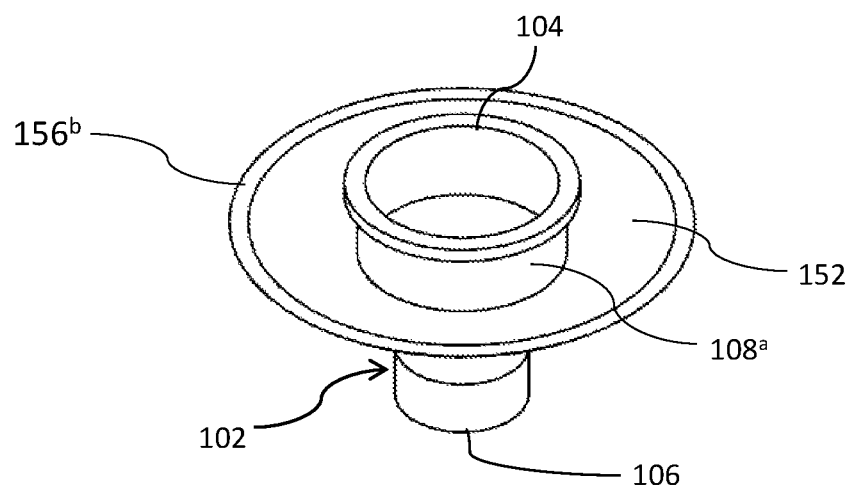
Figure 8:
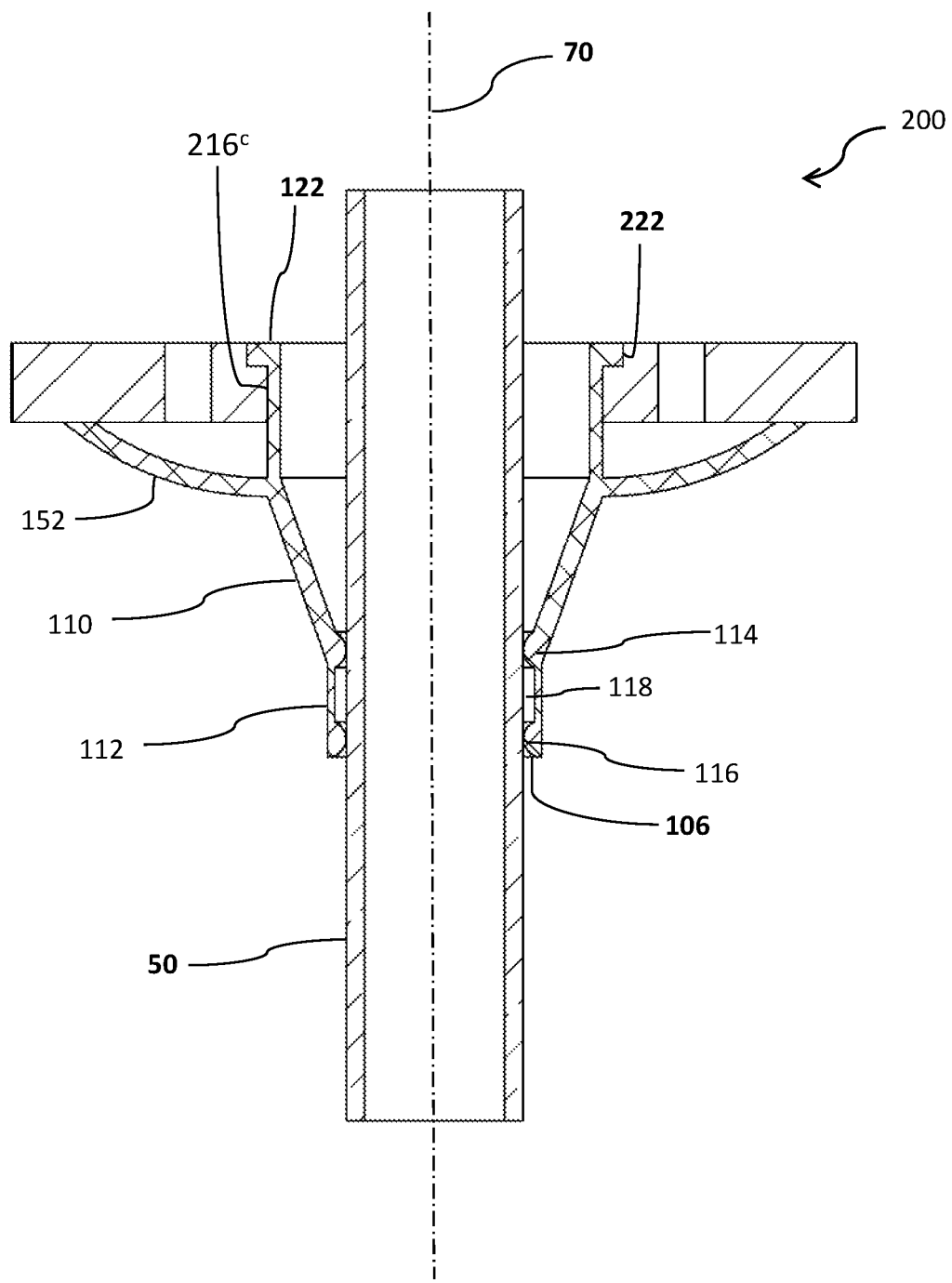

FIG. 8 shows a cross-sectional view of the sealing valve of FIG. 6 mounted within a container wall having a bore recess, according to some implementations.

Figure 9:
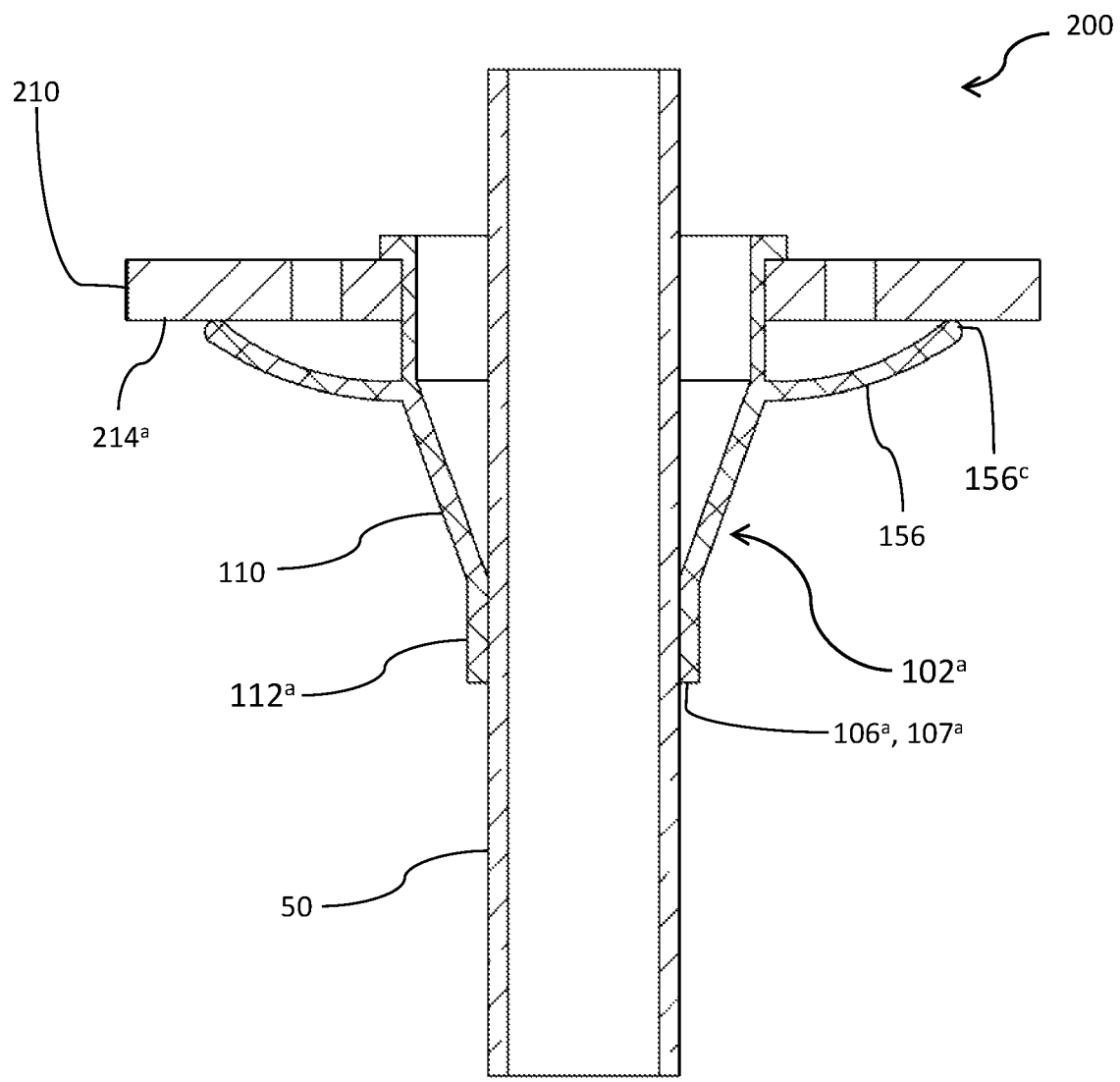

FIG. 9 shows a cross-sectional view of a sealing assembly, including a sealing valve provided with a rounded membrane lip, according to some implementations.

Figure 10:
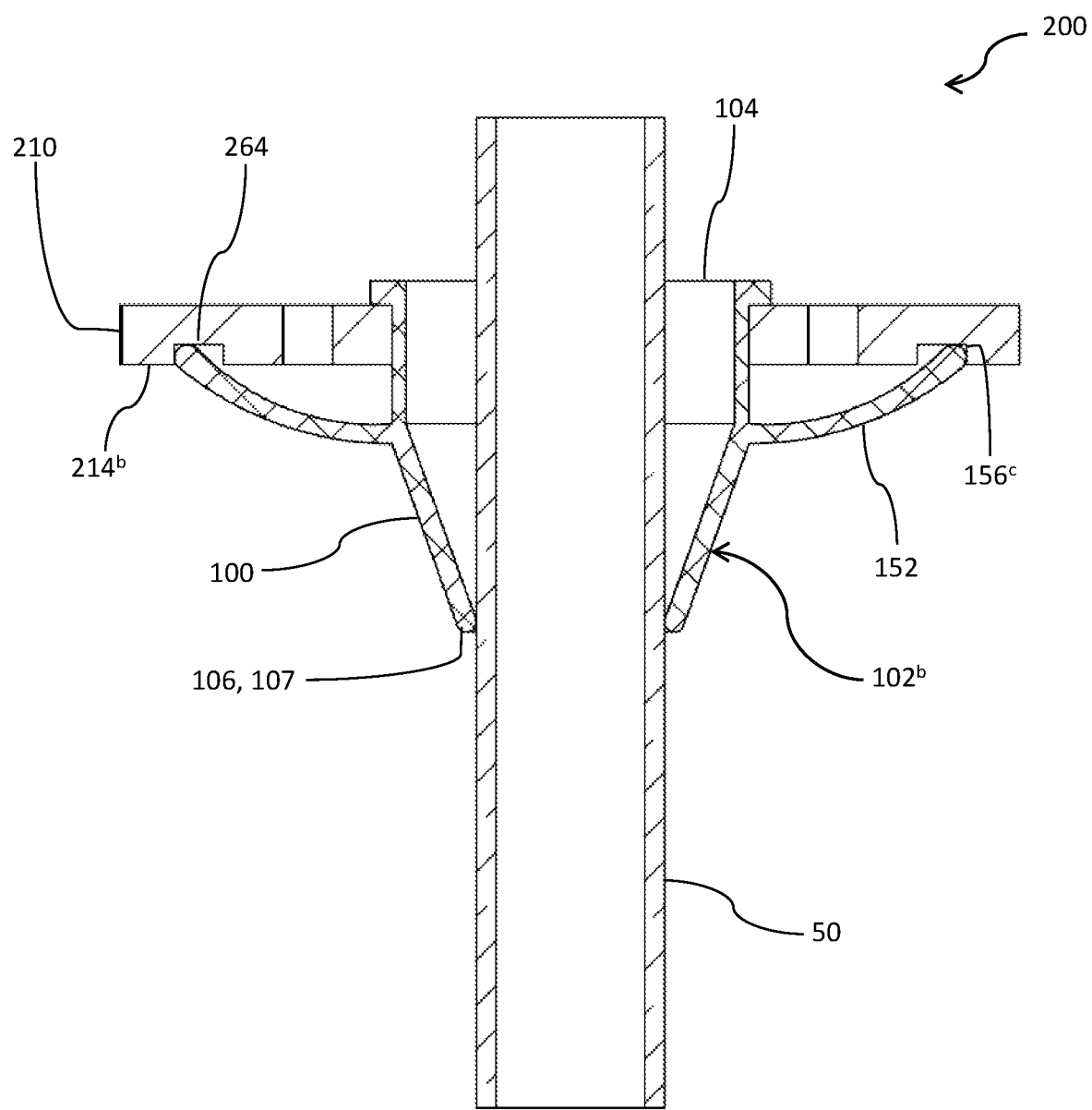

FIG. 10 shows a cross-sectional view of a sealing assembly, including a sealing valve devoid of an annular distal segment, mounted within a container wall having a receiving channel, according to some implementations.

Figure 11A:
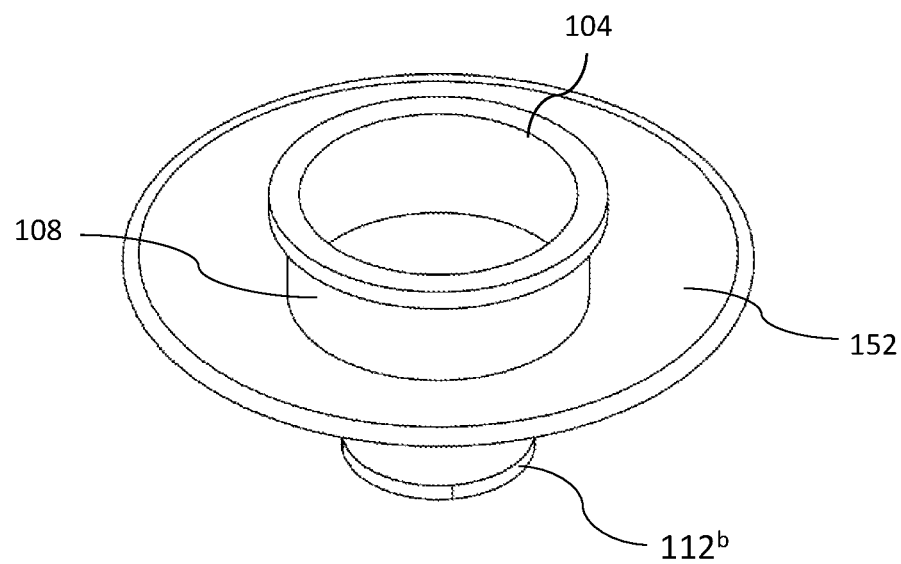

FIG. 11A shows a perspective view from a top-side angle of a sealing valve provided with distal flaps, in a distal free state, according to some implementations.

Figure 11B:
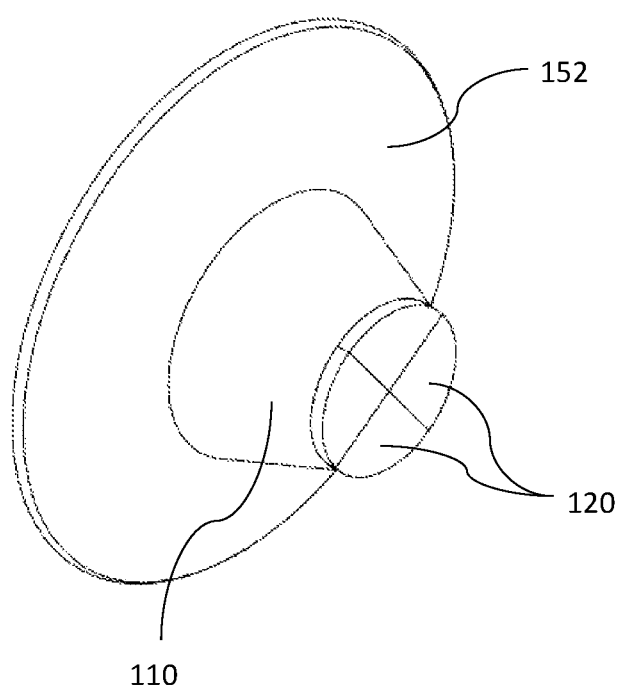

FIG. 11B shows a perspective view from a down-side angle of the sealing valve of FIG. 11A.

Figure 11C:
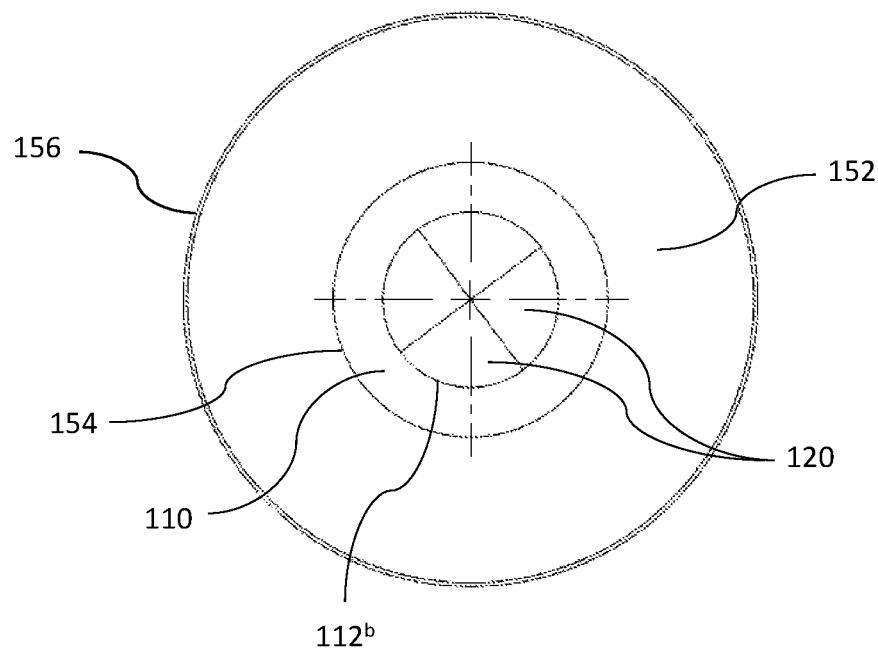

FIG. 11C shows a distal elevation view of the sealing valve of FIG. 11A.

Figure 11D:
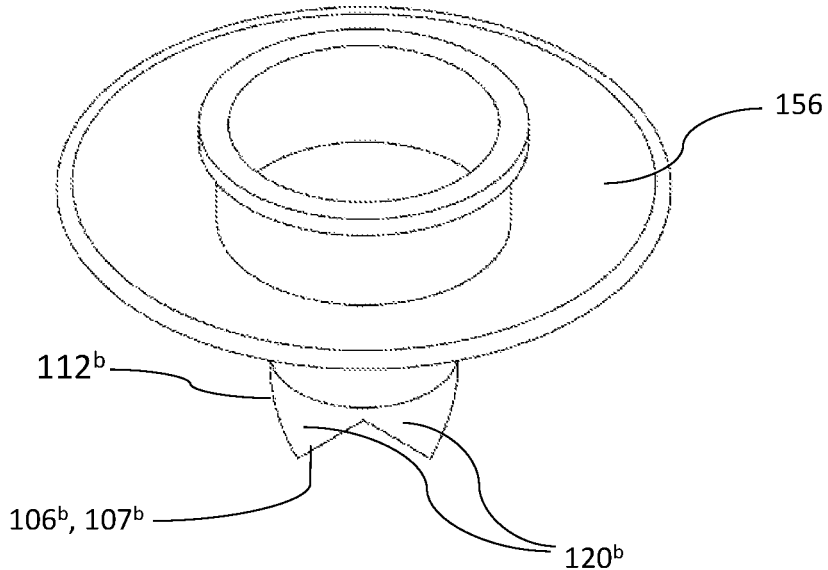

FIG. 11D shows a perspective view of the sealing valve of FIG. 11A in a distal sealed or open state.

Figure 12A:
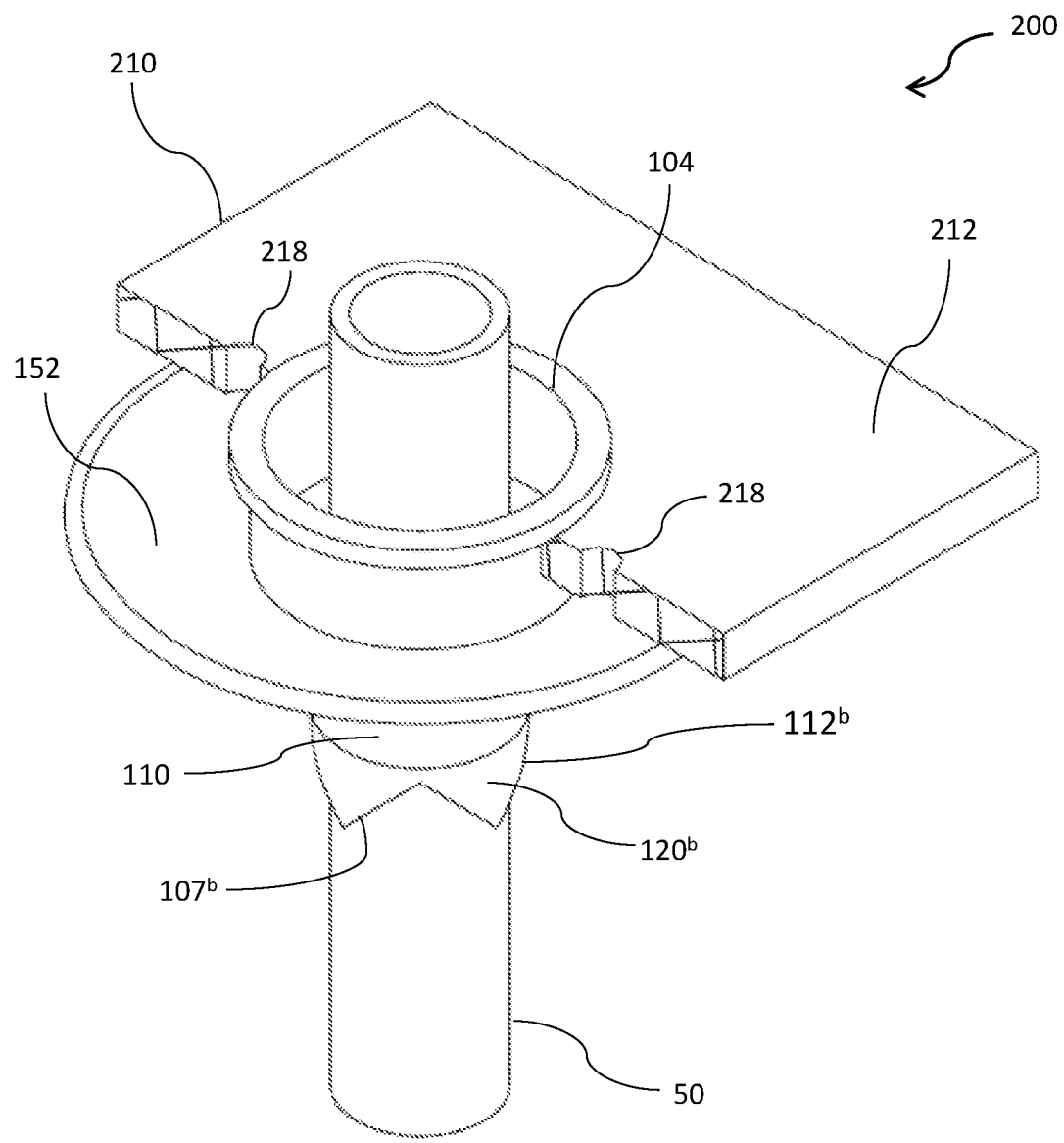

FIG. 12A shows a perspective view of a sealing assembly, including the sealing valve of FIG. 11D in a distal sealed state.

Figure 12B:
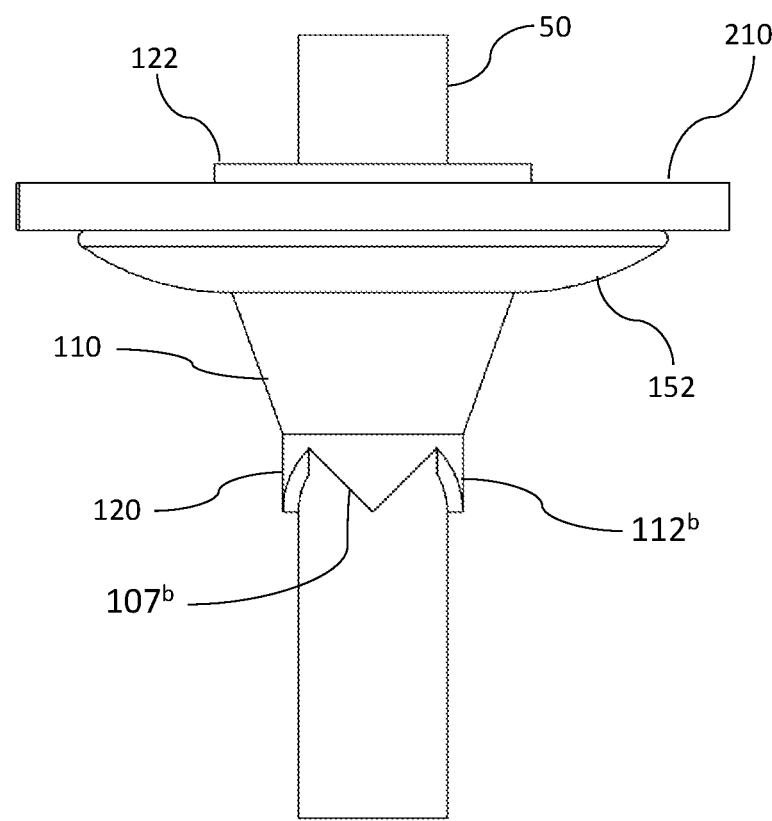

FIG. 12B shows a side view of the sealing assembly of FIG. 12A.

Figure 13A:
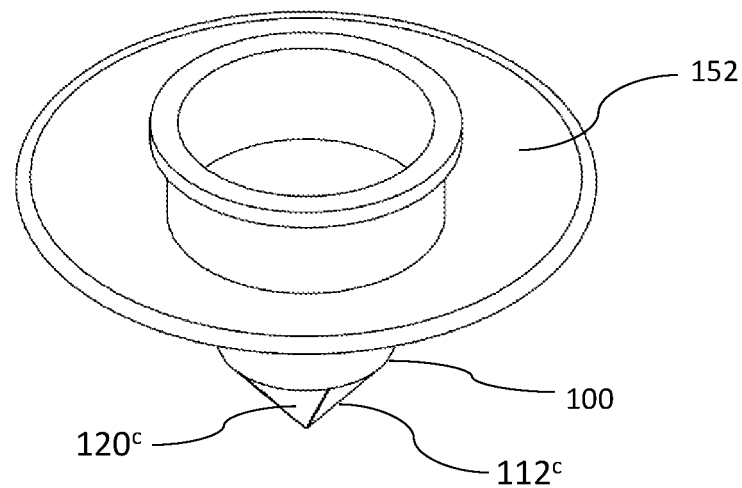

FIG. 13A shows a perspective view from a top-side angle of a sealing valve provided with distal flaps, according to some implementations.

Figure 13B:
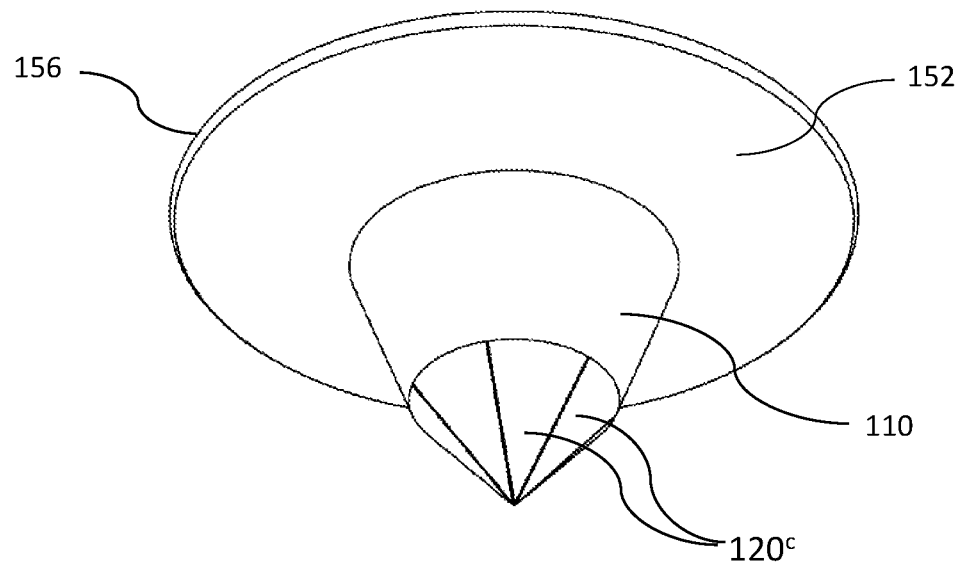

FIG. 13B shows a perspective view from a down-side angle of the sealing valve of FIG. 13A.

Figure 13C:
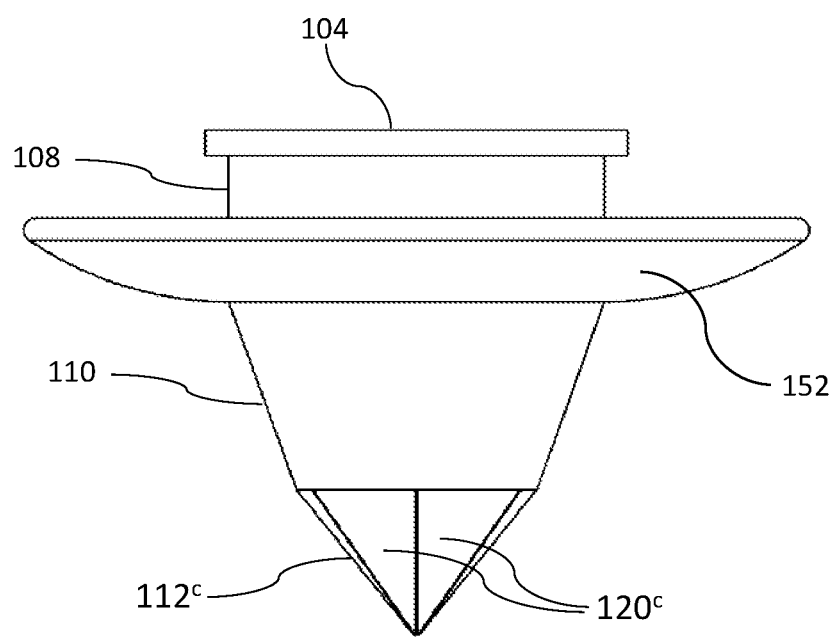

FIG. 13C shows a side view of the sealing valve of FIG. 13A.

Figure 14A:
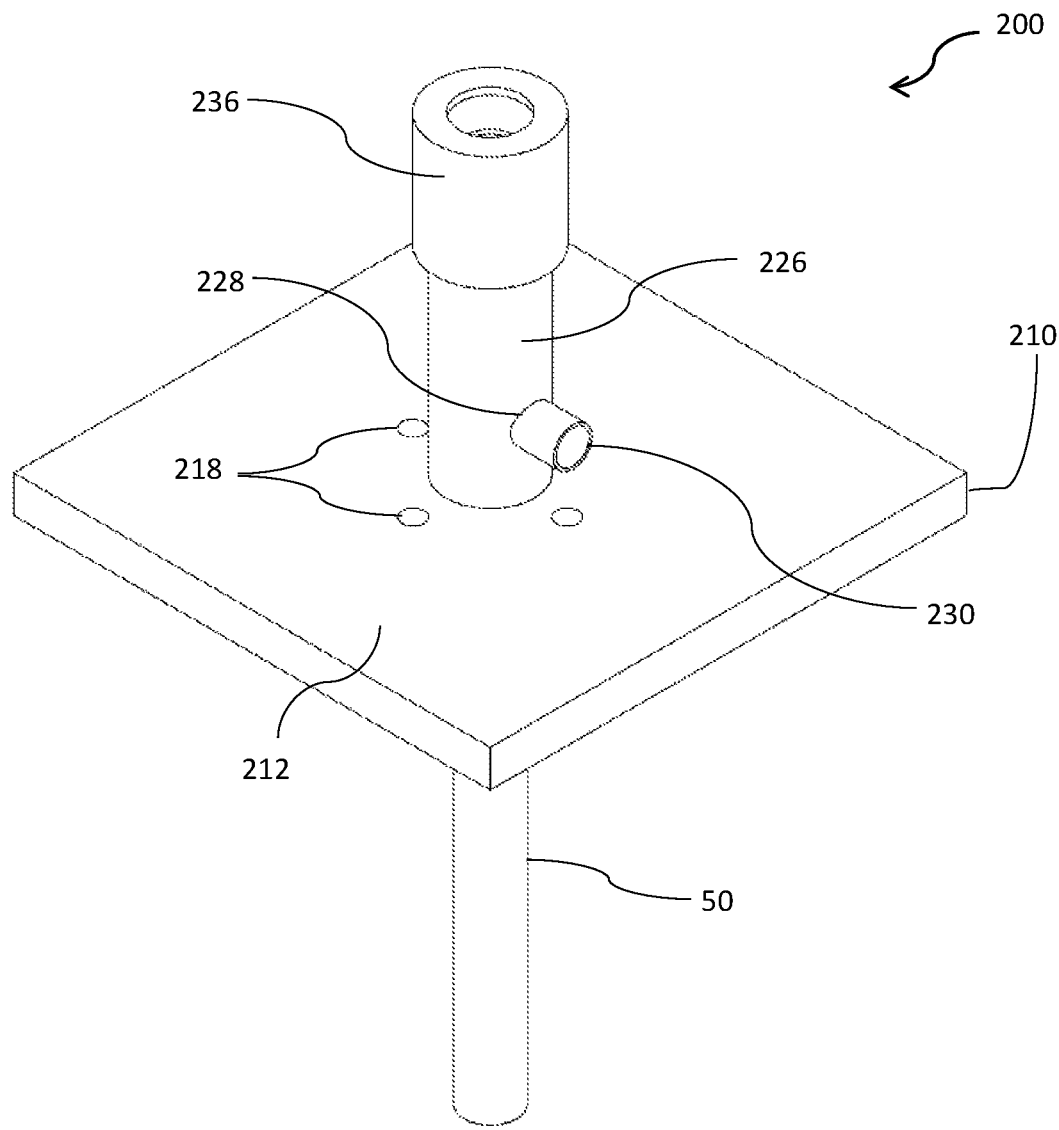

FIG. 14A shows a perspective view of a sealing assembly, wherein the container wall includes a hollow extension, according to some implementations.

Figure 14B:
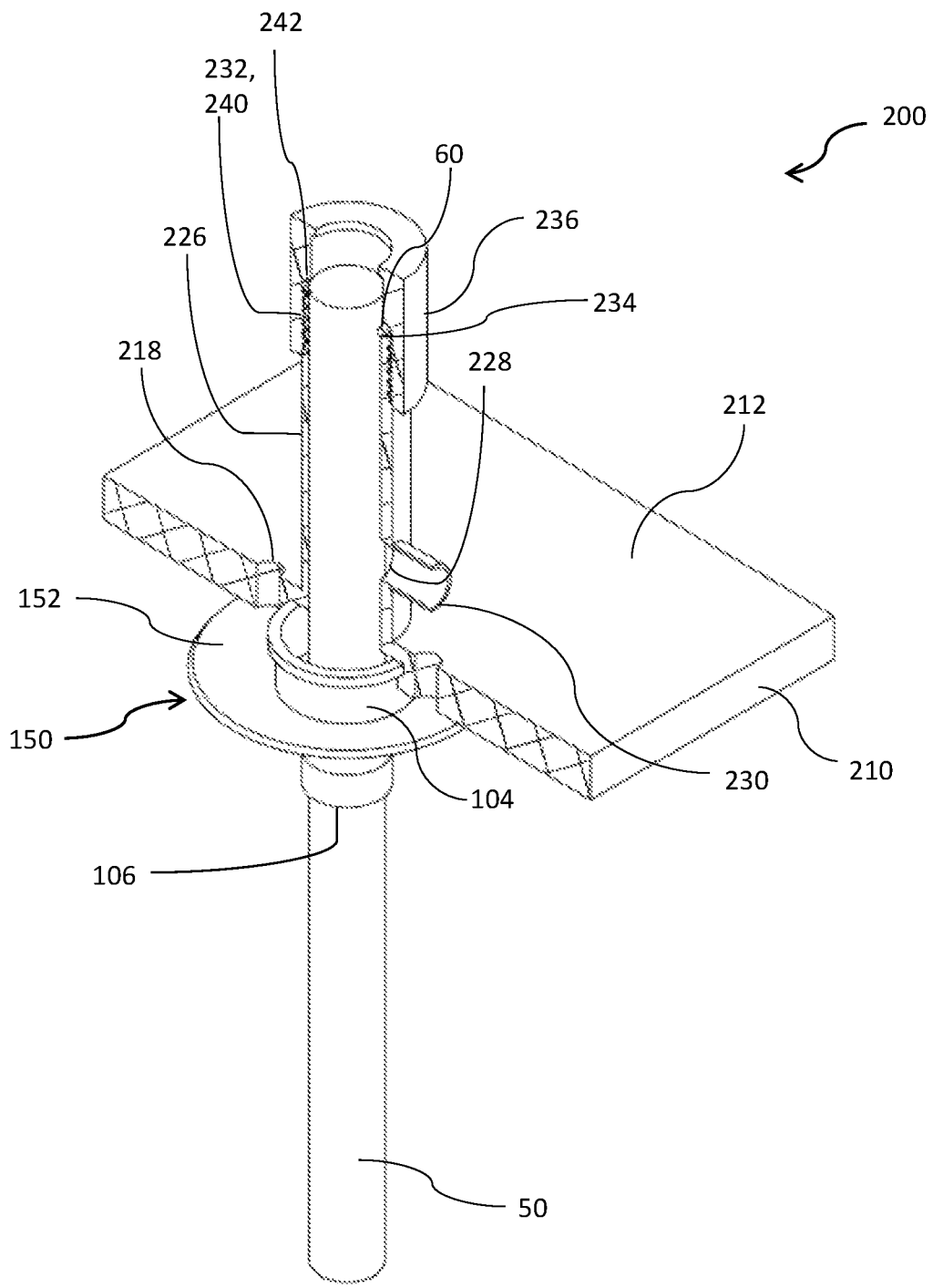

FIG. 14B shows a partial cutaway view in perspective of the sealing assembly of FIG. 14A.

Figure 15:
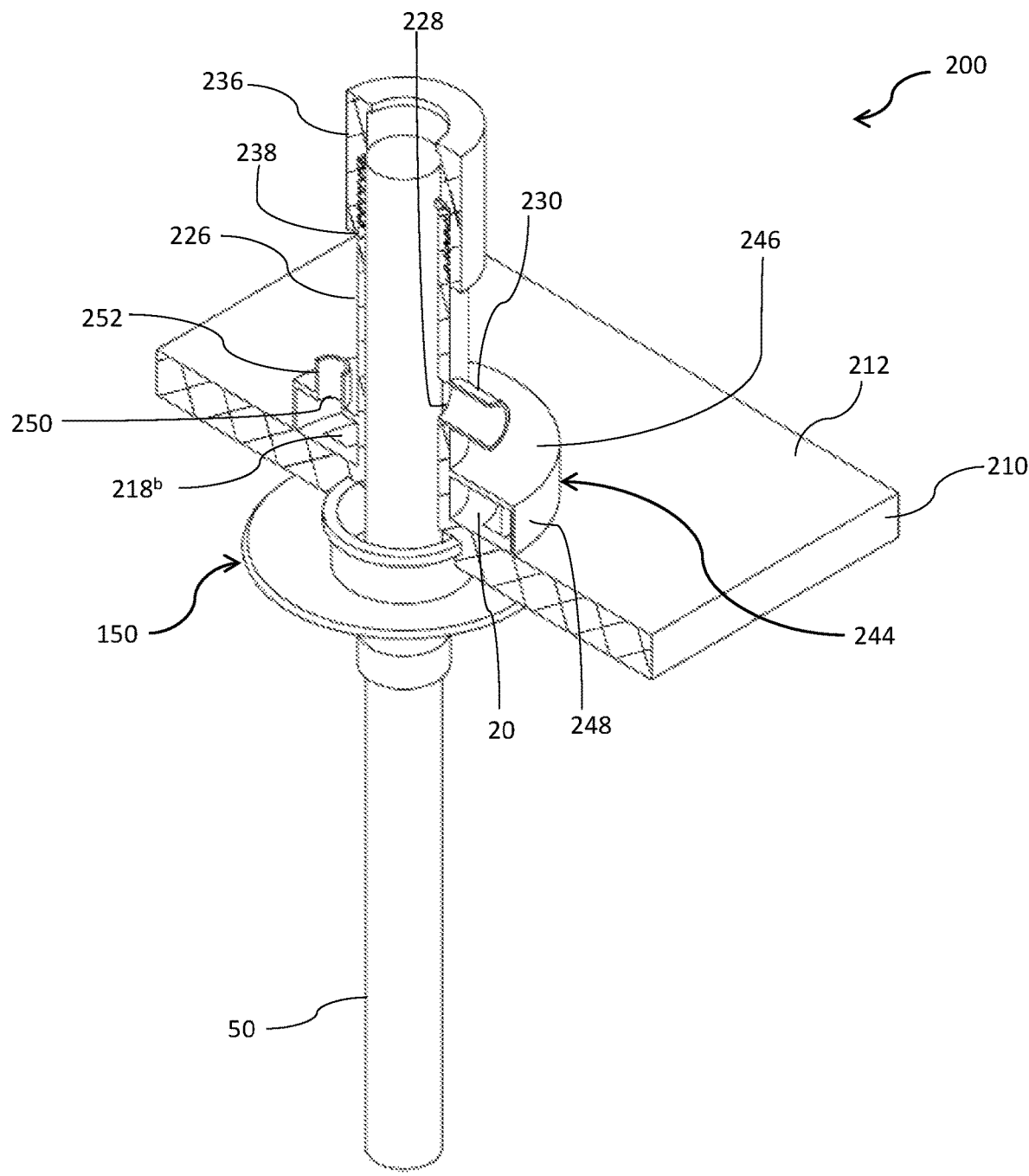

FIG. 15 shows a perspective view of a sealing assembly, wherein the container wall includes a peripheral inlet chamber, according to some implementations.

Figure 16:
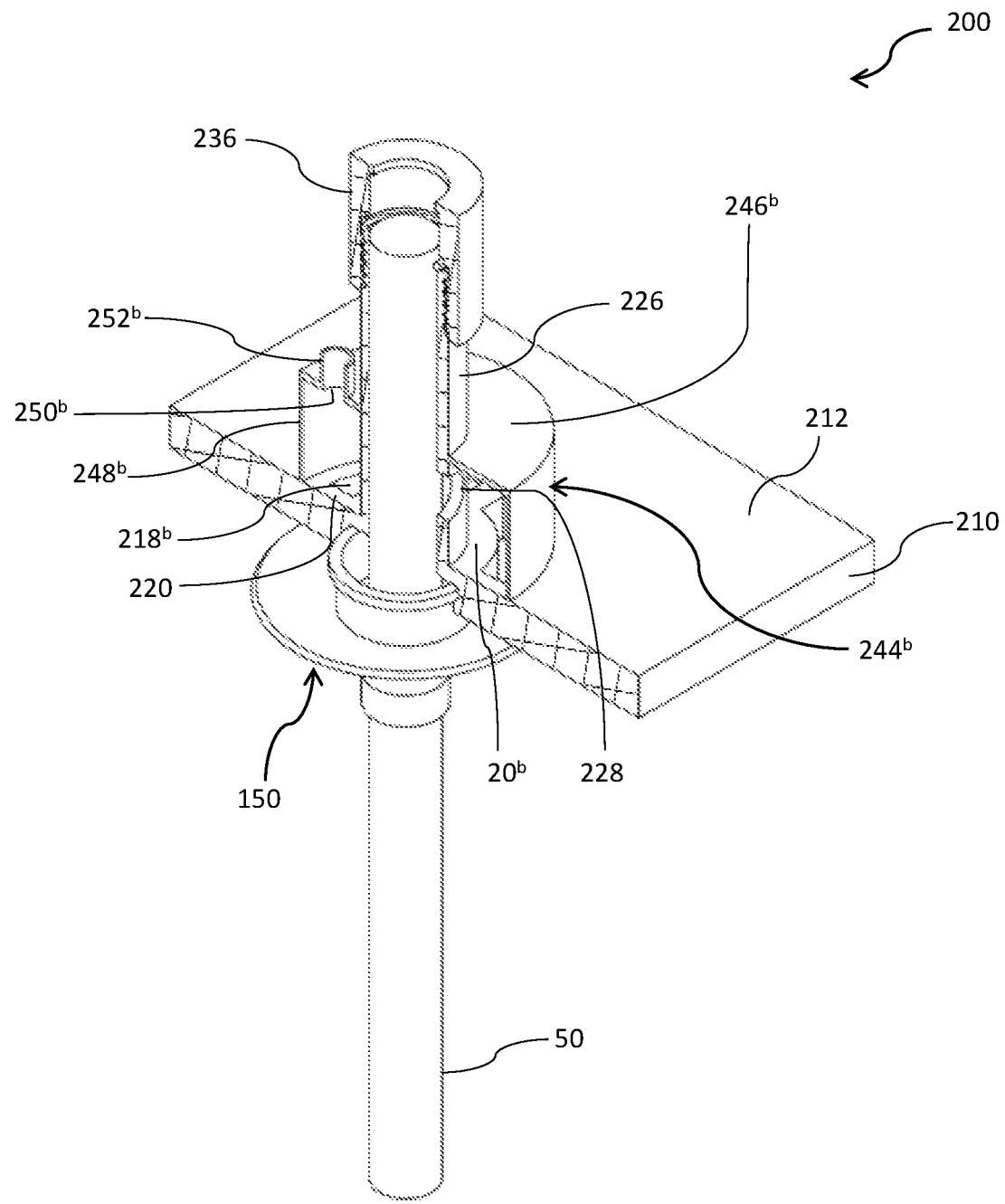

FIG. 16 shows a perspective view of a sealing assembly, wherein the container wall includes another variant of a peripheral inlet chamber, according to some implementations.

Figure 17:
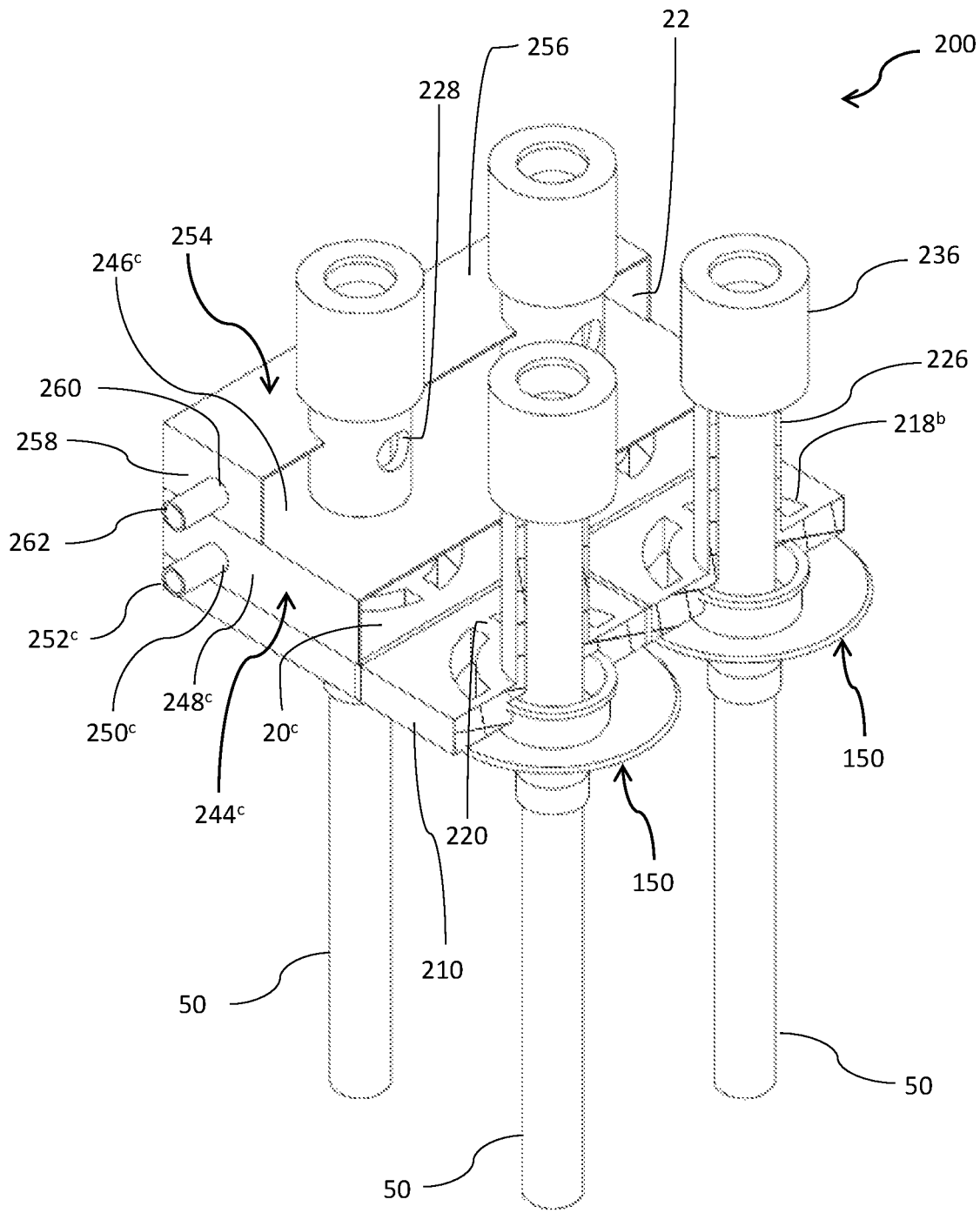

FIG. 17 shows a partial cutaway view in perspective of a plurality of sealing valves mounted within a container wall having a peripheral inlet chamber and a central inlet chamber, according to some implementations.

Figure 18:
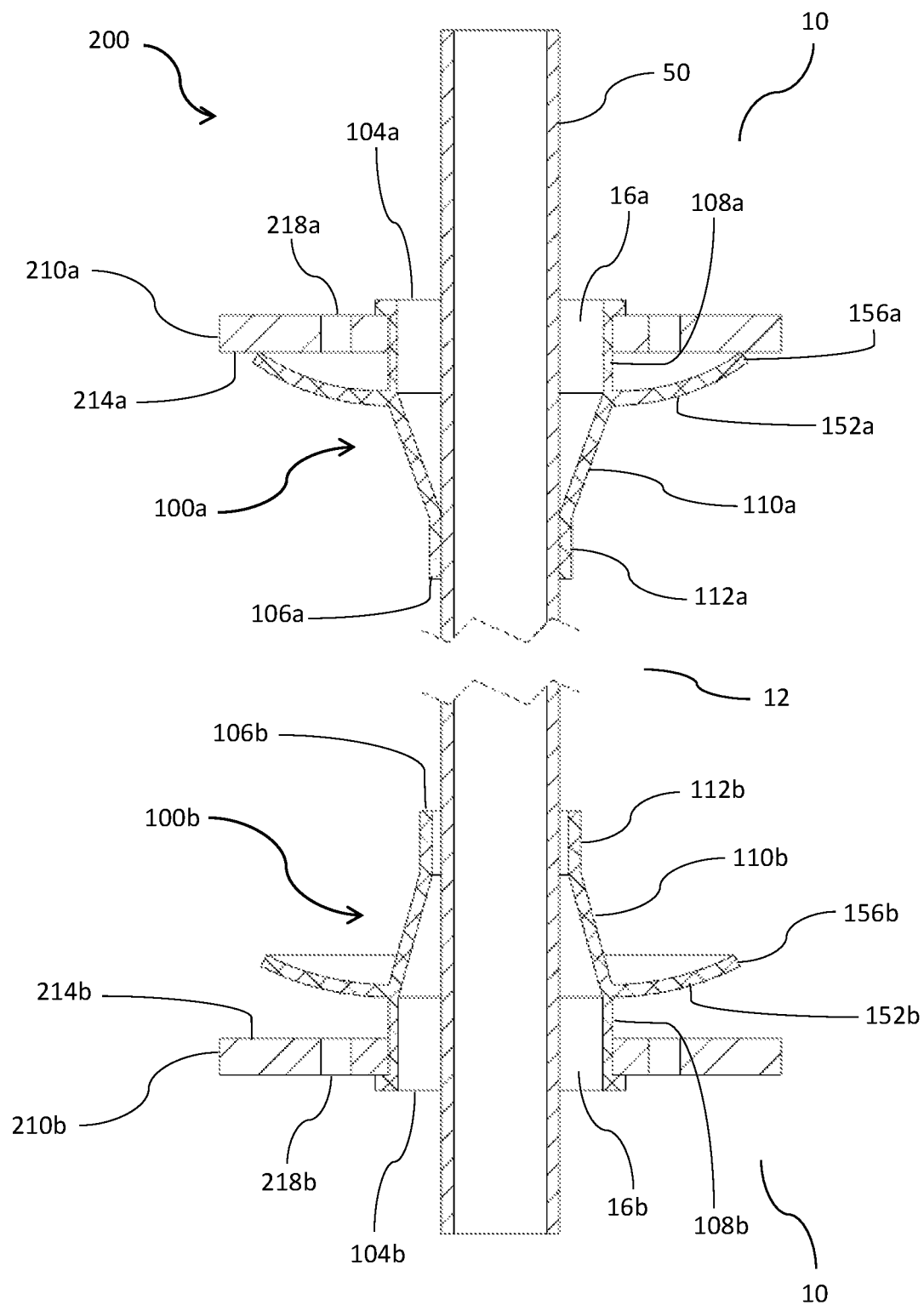

FIG. 18 shows an exemplary configuration of sealing valves mounted within opposing container walls, devoid of hollow extensions.

Figure 19:
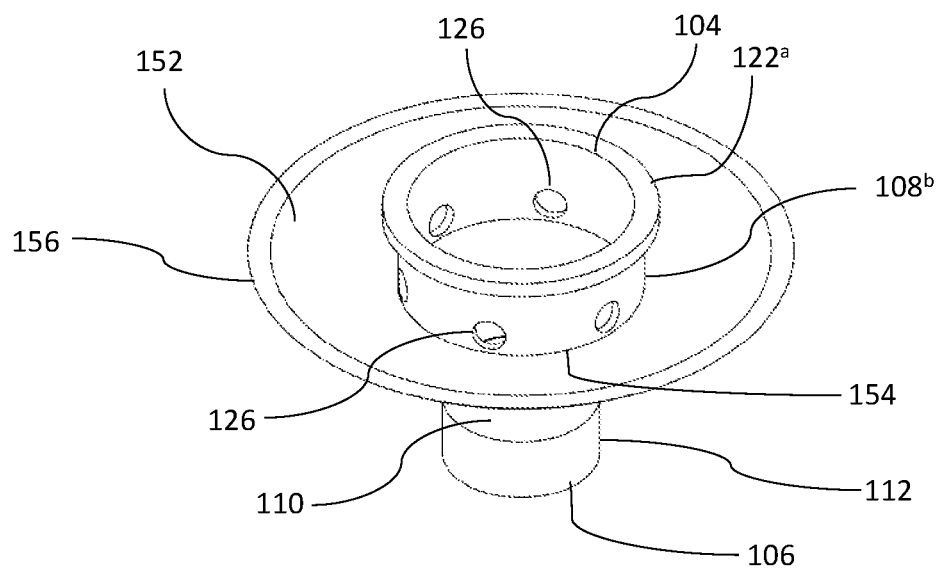

FIG. 19 shows a view in perspective of a sealing valve with side openings, according to some implementations.

Figure 20:
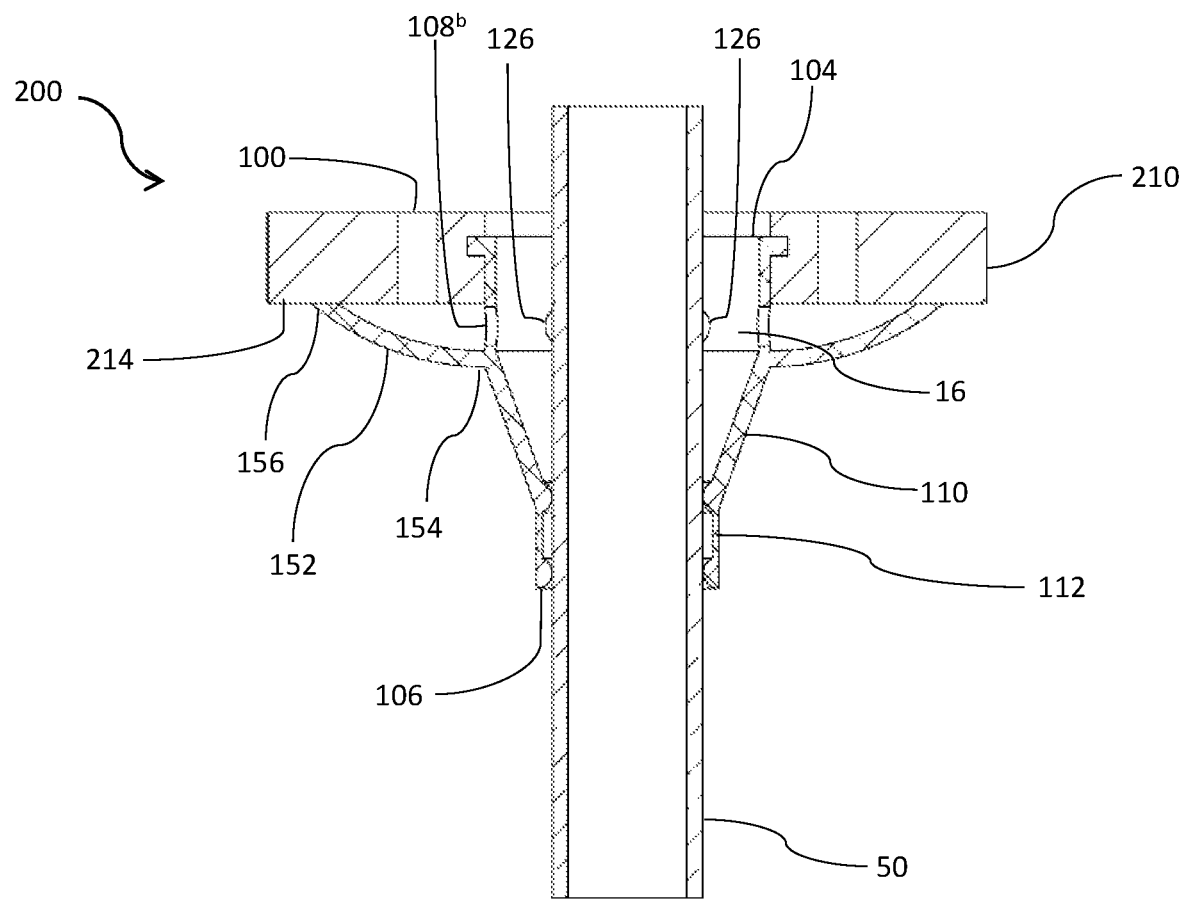

FIG. 20 shows a sealing assembly, including the sealing valve of FIG. 19 in a peripheral sealed state and a distal sealed state thereof.

Figure 21:
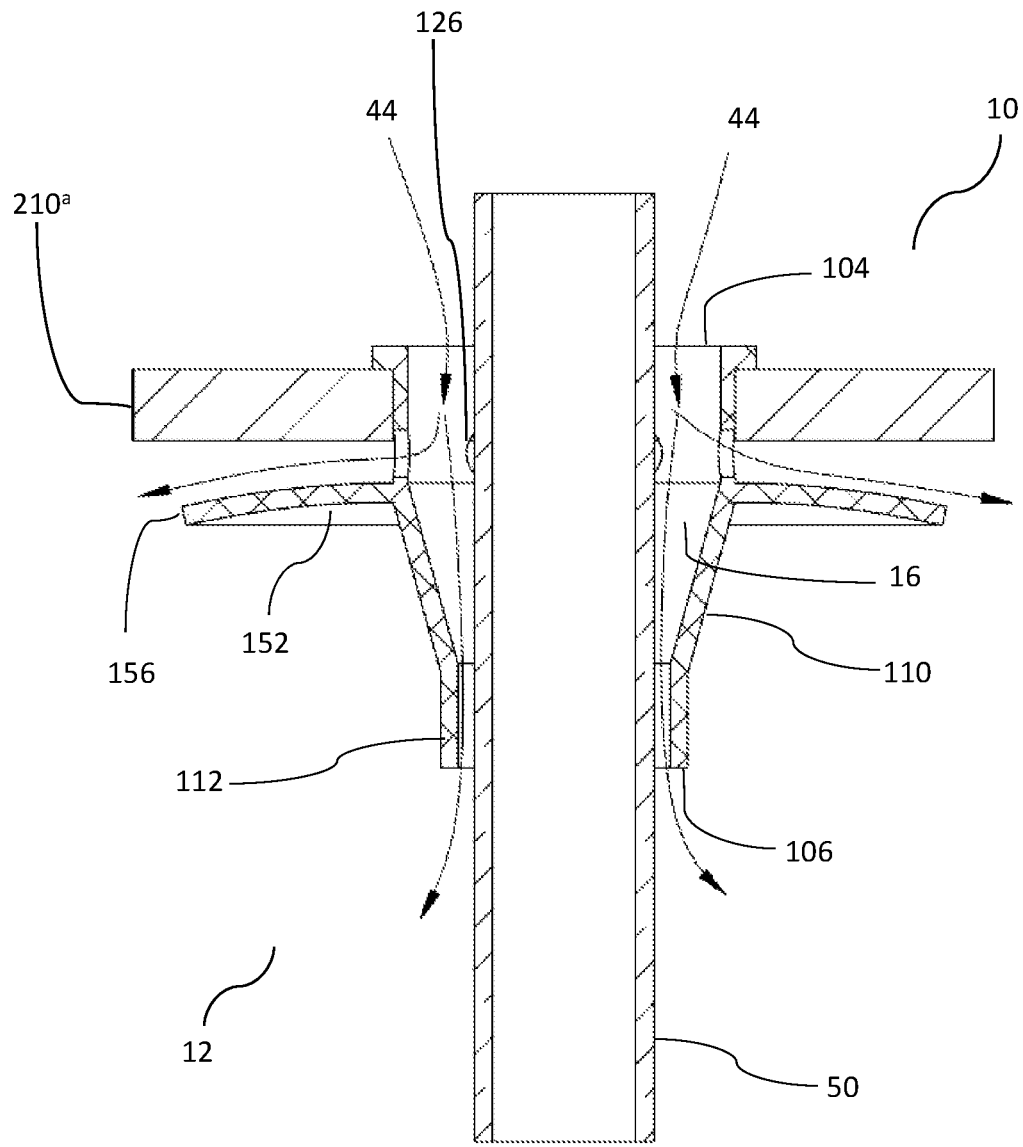

FIG. 21 shows a sealing assembly, including a container wall devoid of peripheral openings, and the sealing valve of FIG. 19 in a peripheral open state and a distal open state thereof.

Figure 22A:
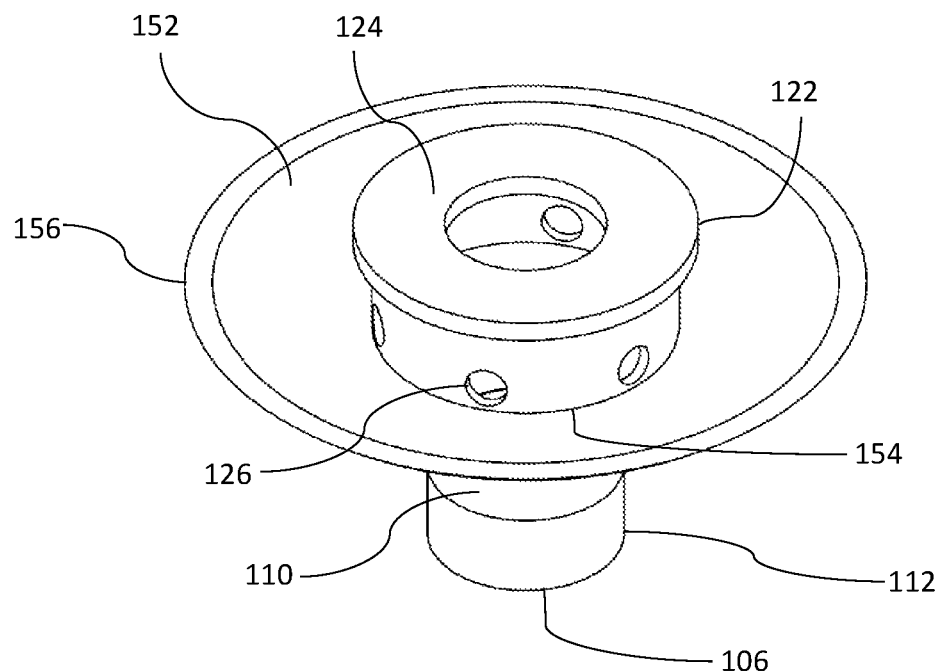

FIG. 22A shows a perspective view of a sealing valve with side openings and a proximal seal, according to some implementations.

Figure 22B:
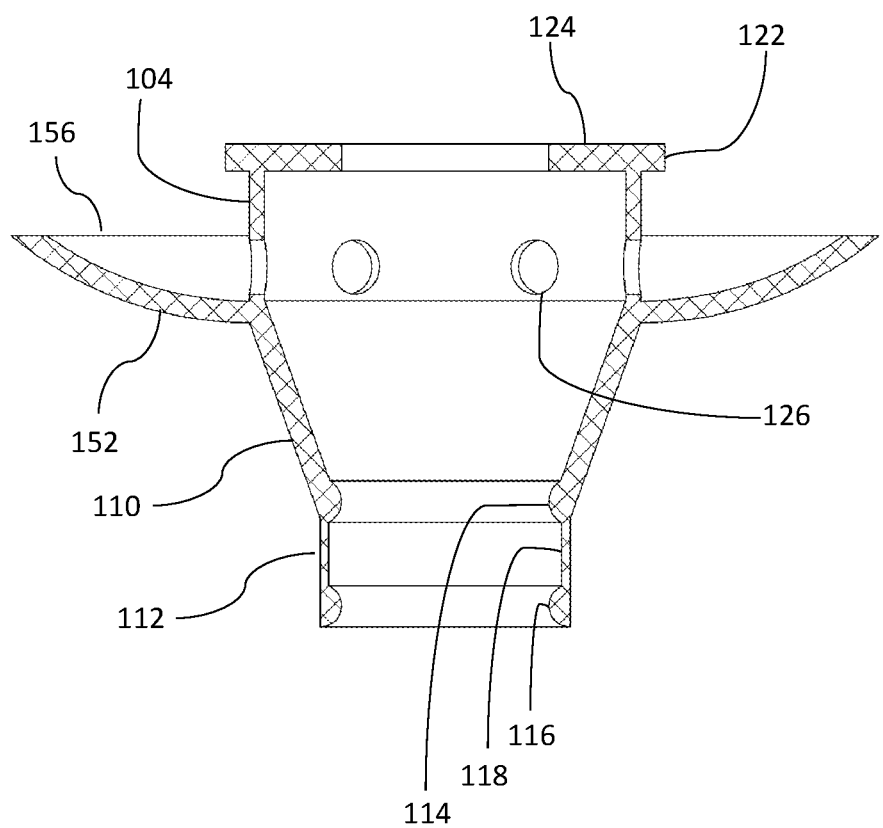

FIG. 22B shows a sectional view in perspective of the sealing valve of FIG. 22A.

Figure 23:
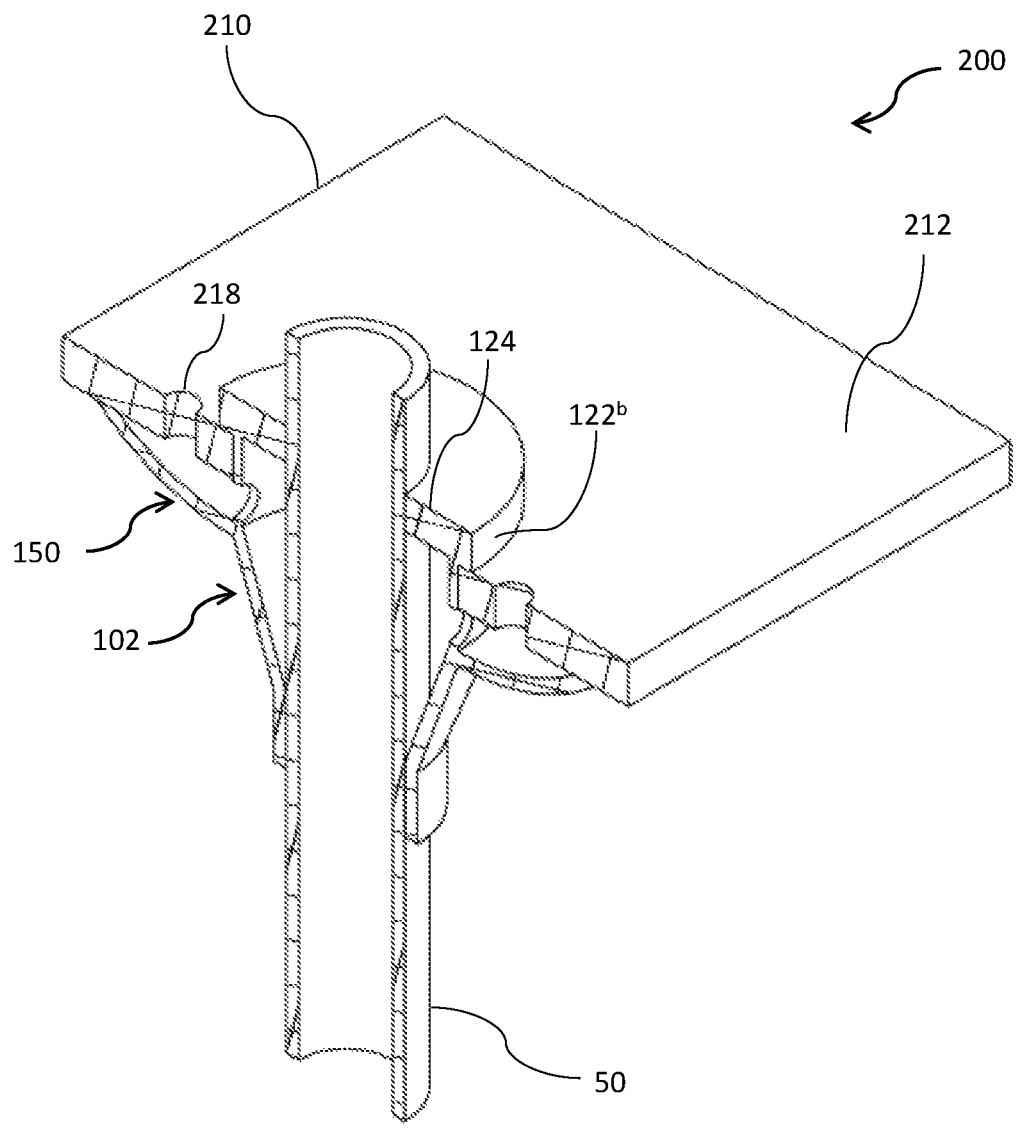

FIG. 23 shows a sealing assembly, including the sealing valve of FIG. 22A.

Figure 24A:
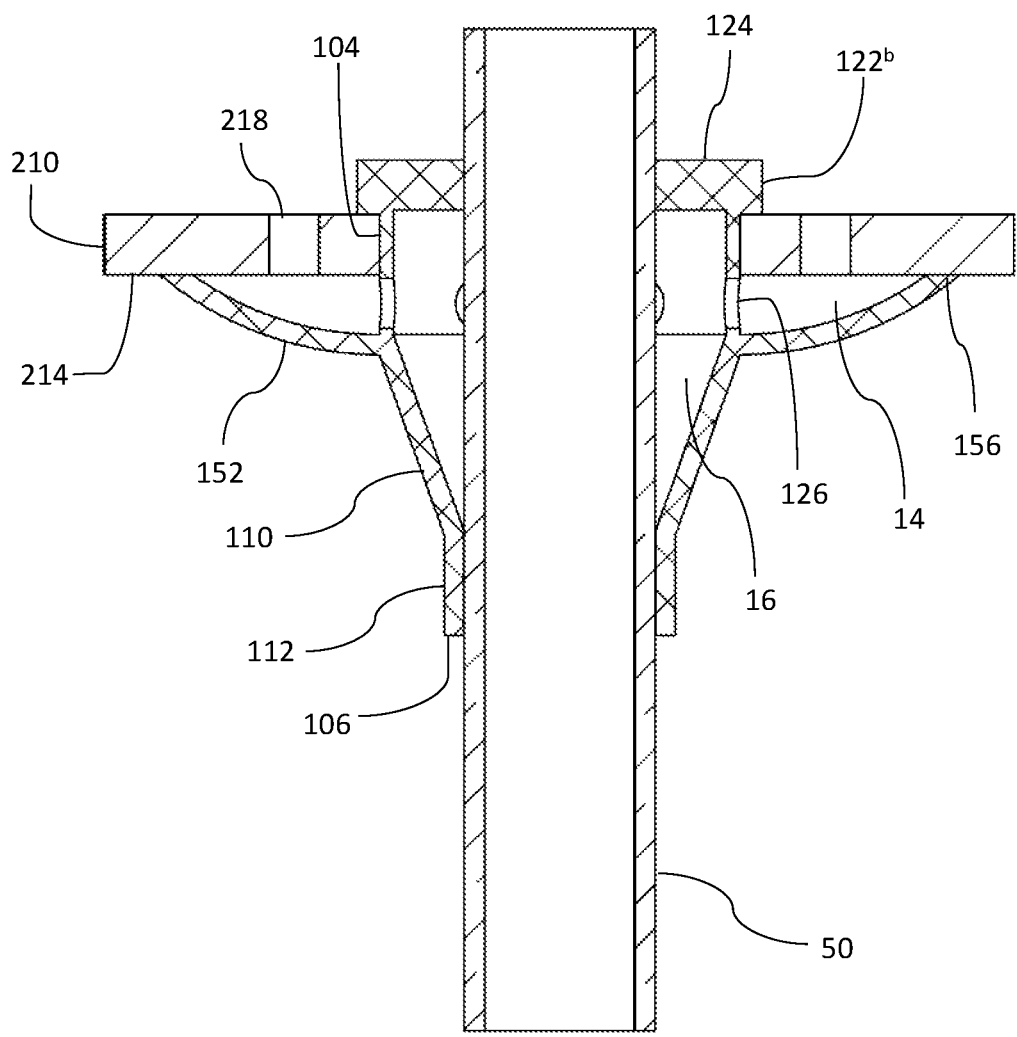

FIG. 24A shows a cross-sectional view of the sealing assembly of FIG. 23, in a peripheral sealed state and a distal sealed state of the sealing valve.

Figure 24B:
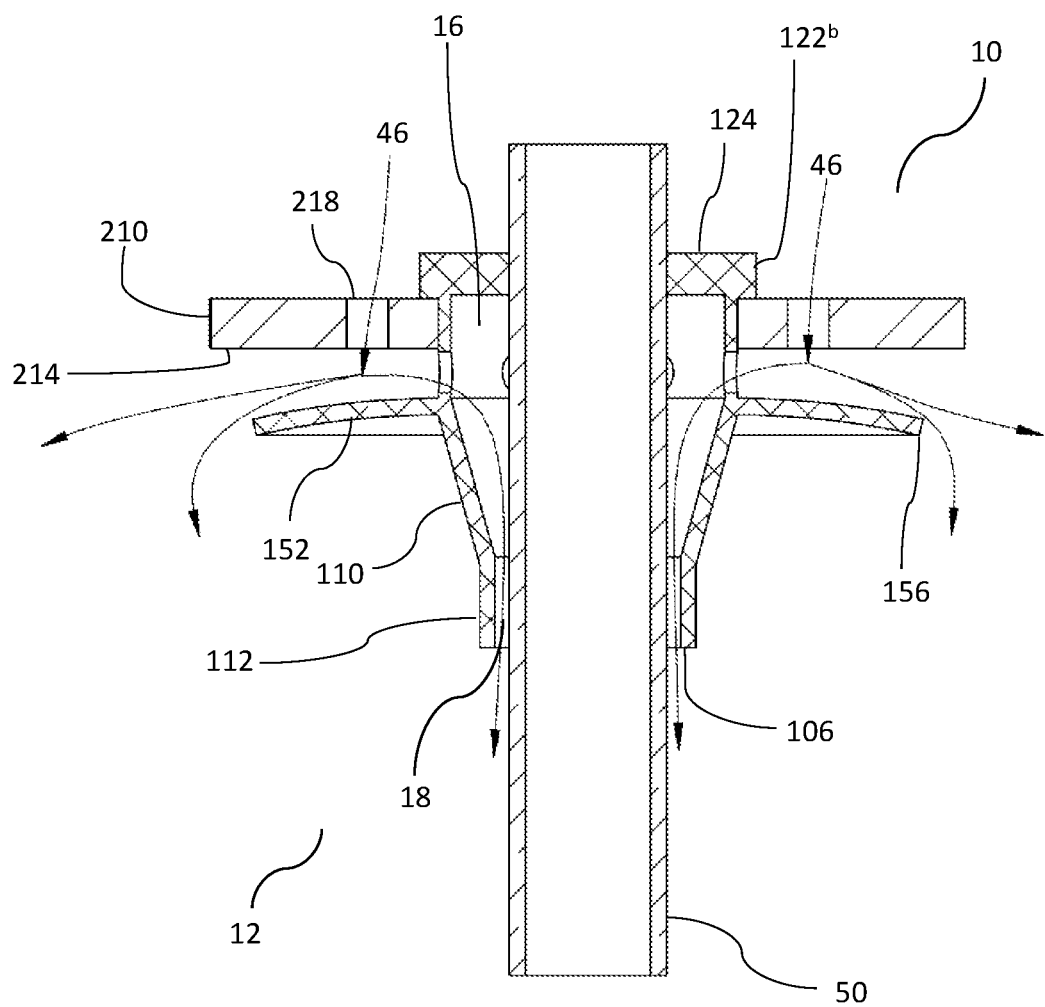

FIG. 24B shows the sealing assembly of FIG. 24A, in a peripheral open state and a distal open state of the sealing valve.

Figure 25:
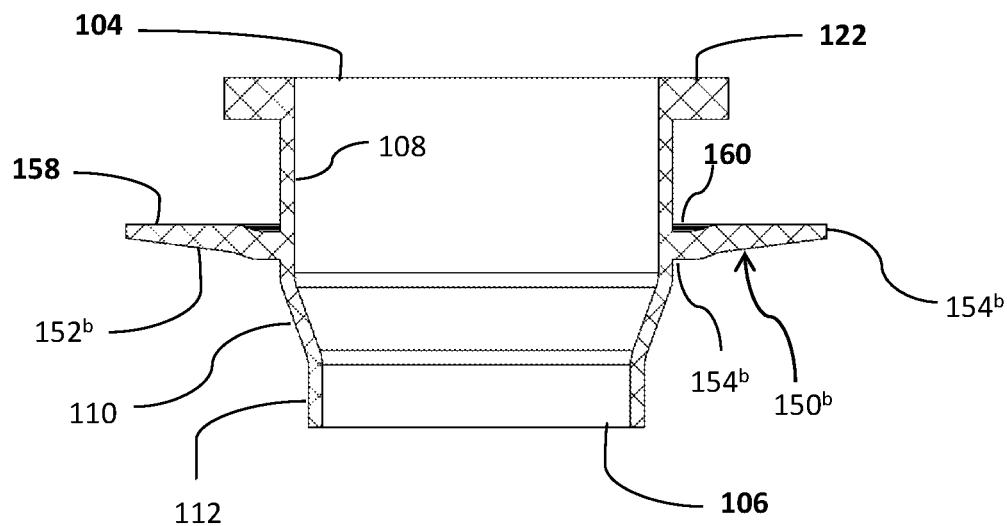

FIG. 25 shows a cross-sectional view of a sealing valve provided with a membrane valve portion having a flat surface section, according to some implementations.

Figure 26A:
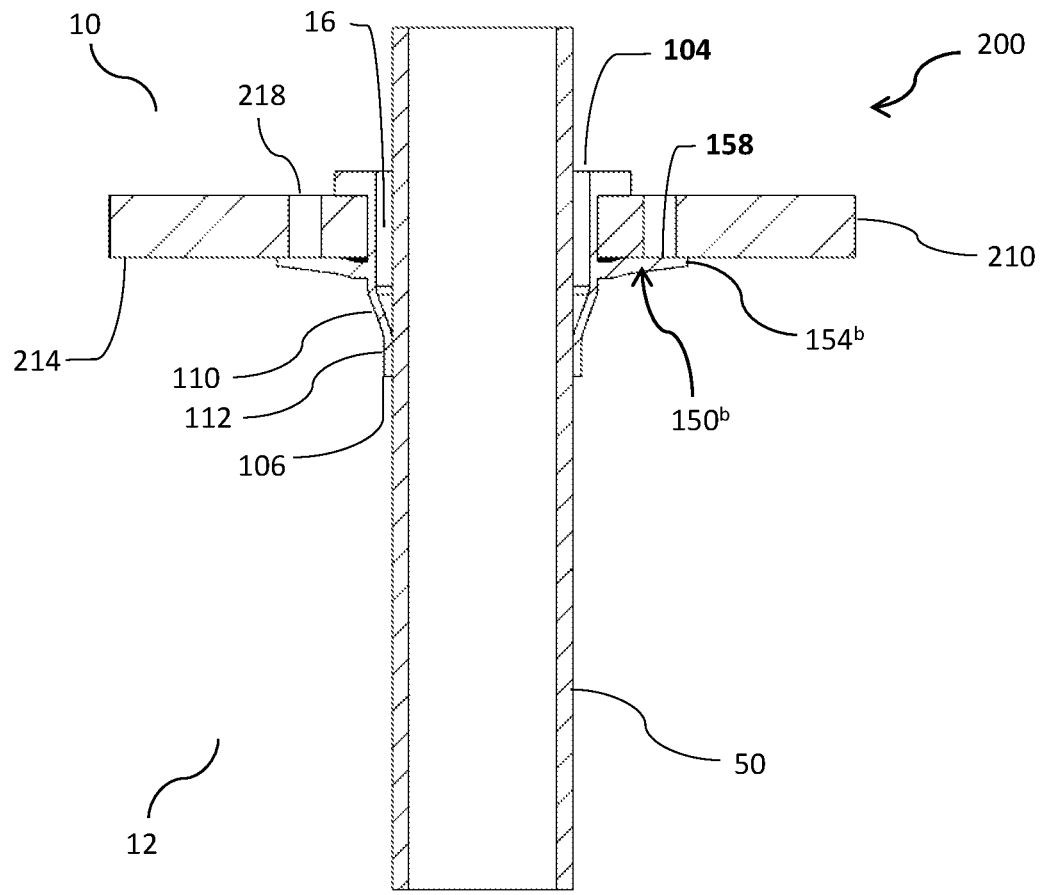

FIG. 26A shows a cross-sectional view of a sealing assembly, including the sealing valve of FIG. 25 in a peripheral sealed state and a distal sealed state.

Figure 26B:
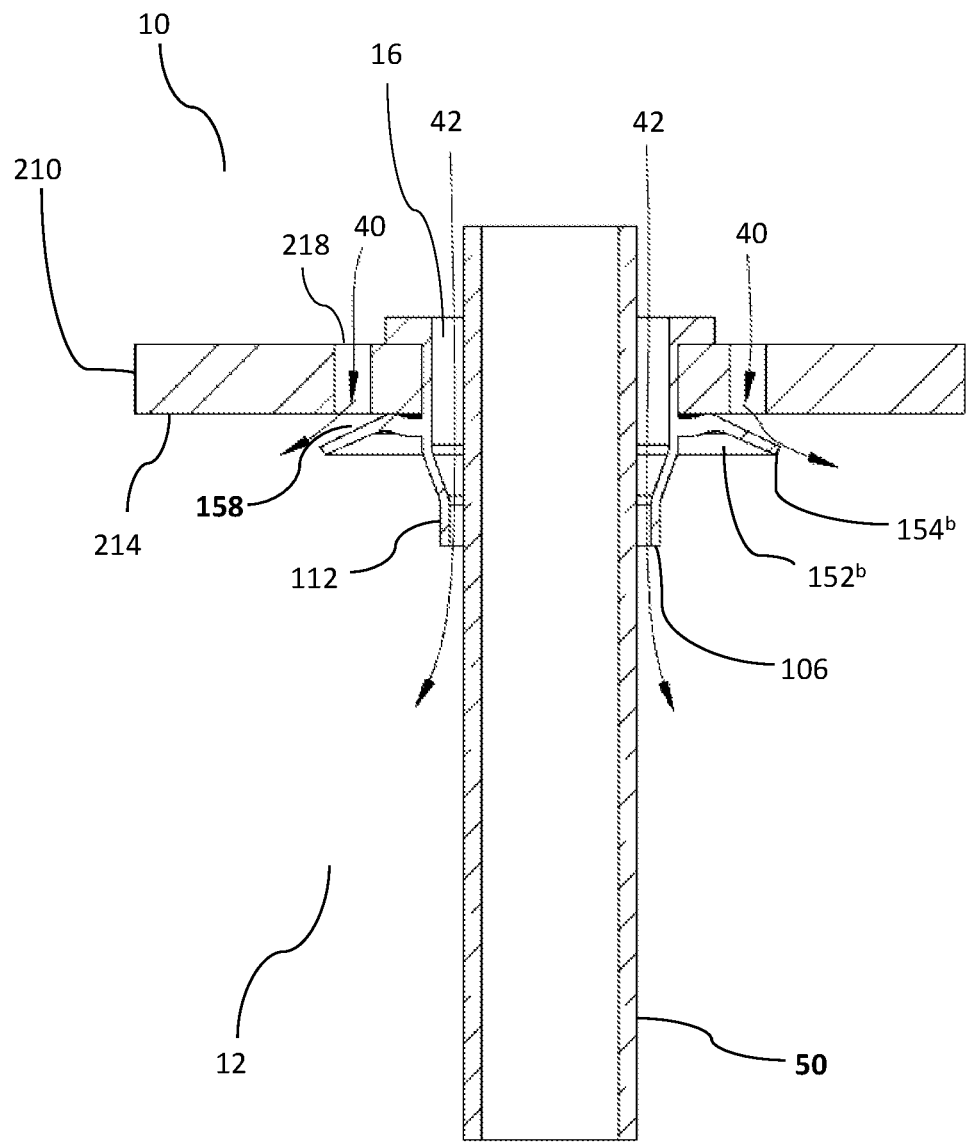

FIG. 26B shows a cross-sectional view of the sealing assembly of FIG. 26B, in a peripheral open state and a distal open state of the sealing valve.

DETAILED DESCRIPTION OF SOME EMBODIMENTS

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure. In order to avoid undue clutter from having too many reference numbers and lead lines on a particular drawing, some components will be introduced via one or more drawings and not explicitly identified in every subsequent drawing that contains that component.

Throughout the figures of the drawings, different superscripts for the same reference numerals are used to denote different embodiments of the same elements. Embodiments of the disclosed devices and systems may include any combination of different embodiments of the same elements. Specifically, any reference to an element without a superscript may refer to any alternative embodiment of the same element denoted with a superscript.

Figure 1A:
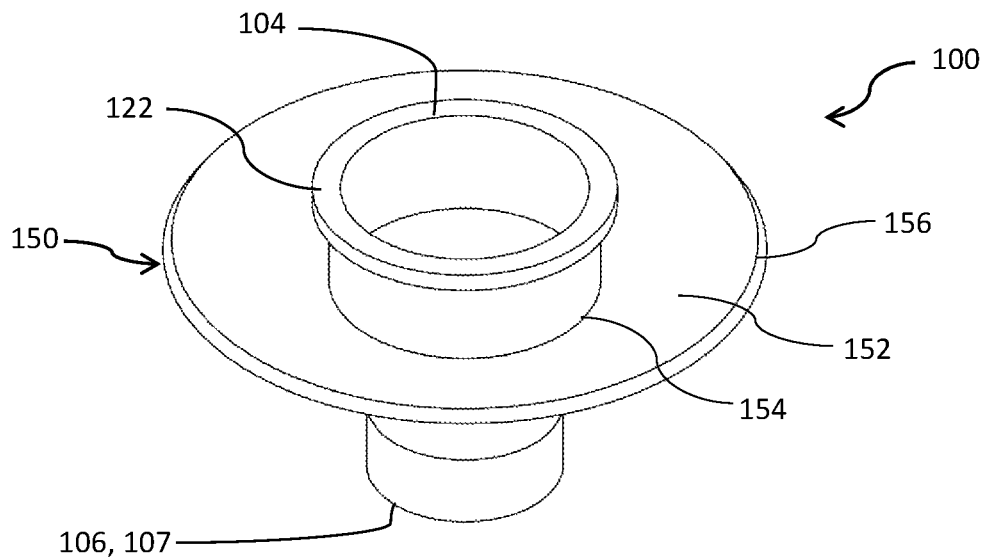
Figure 1B:
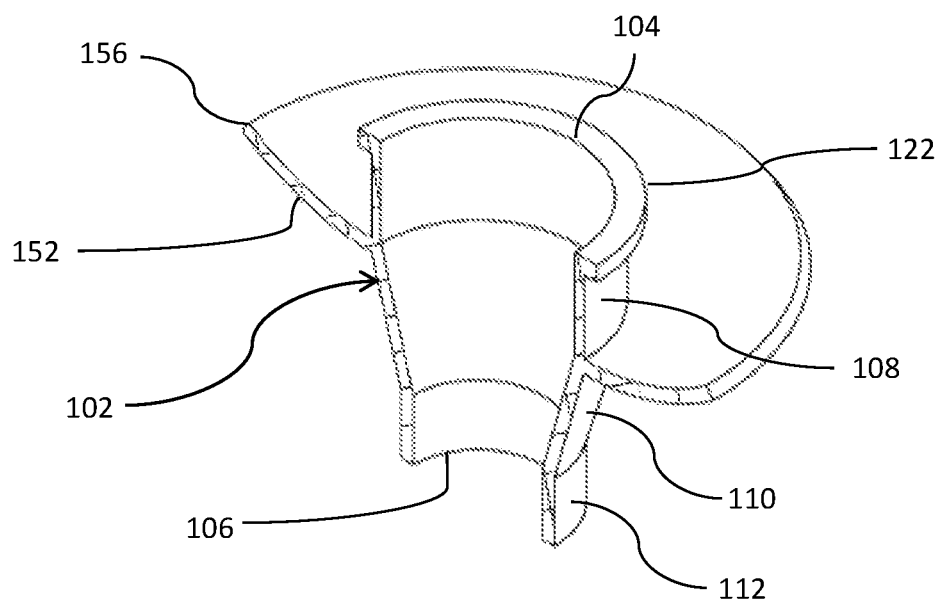
Figure 2A:
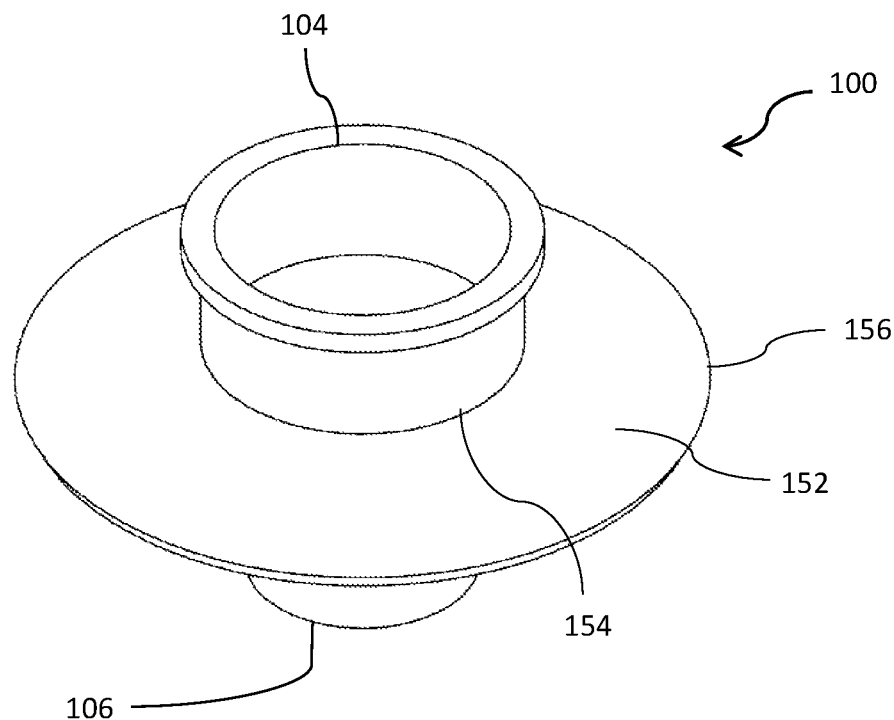
Figure 2B:
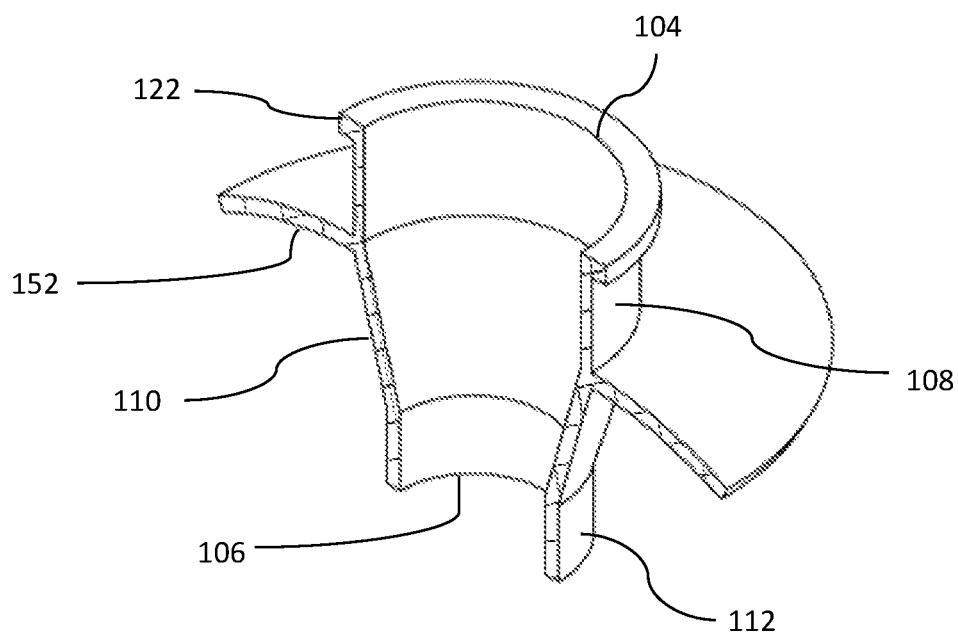
Figure 3:
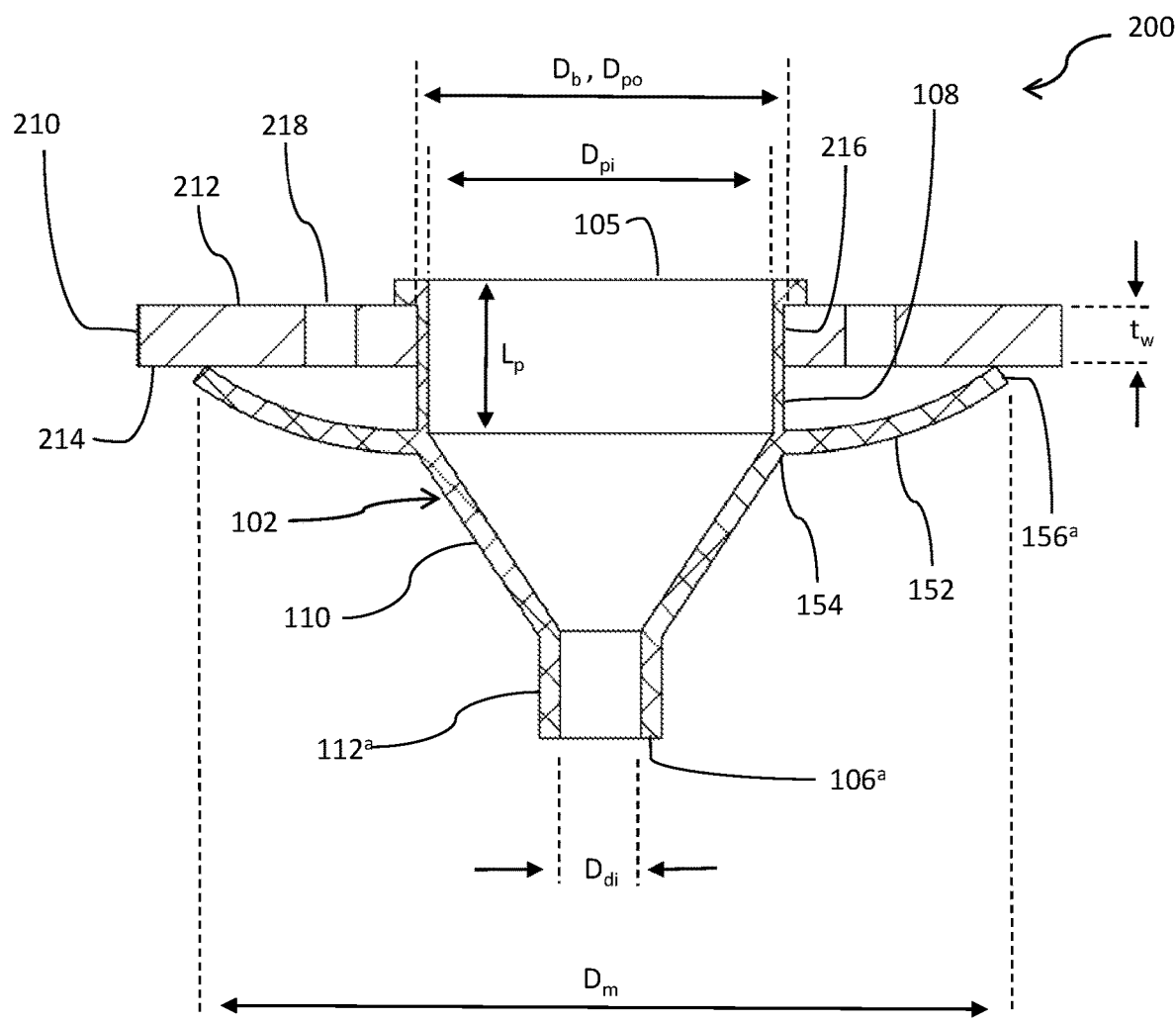
Figure 4:
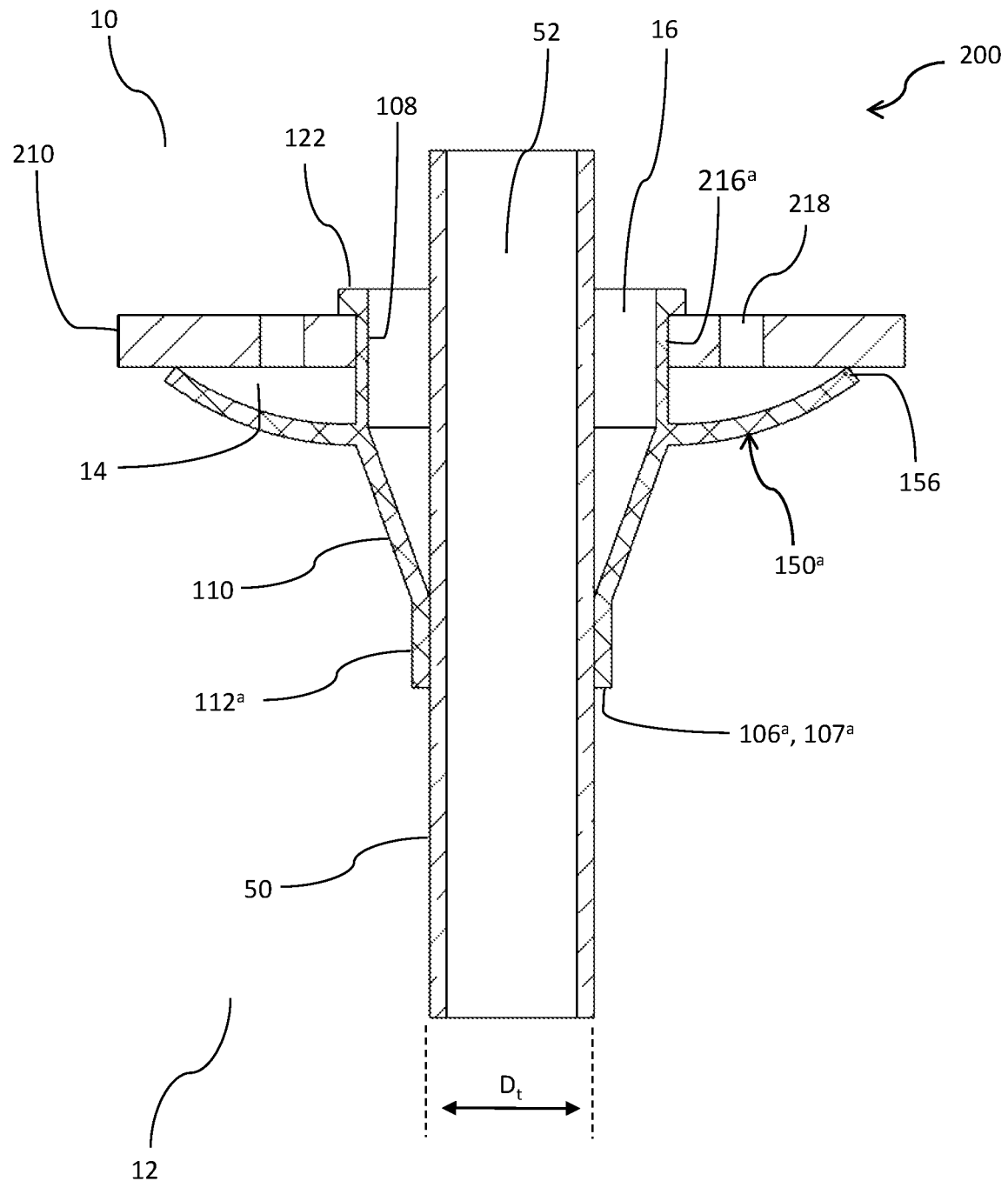

Reference is now made to FIGS. 1-4. FIGS. 1A and 1B show a perspective view and a sectional view in perspective of a sealing valve 100 in a peripheral free state, according to some implementations. FIGS. 2A and 2B show a perspective view and a sectional view in perspective of the sealing valve 100 of FIGS. 1A-1B, in a peripheral open state. FIG. 3 shows a cross-sectional view of a sealing assembly 200 that includes a sealing valve 100 mounted within a container wall 210, according to some implementations. FIG. 4 shows a cross-sectional view of the sealing assembly 200 of FIG. 3, having a tube 50 extending longitudinally through the sealing valve 100.

The terms "including" and/or "having", as used herein, are defined as comprising (i.e., open language).

The sealing valve 100 comprises a main body 102, extending longitudinally between a proximal end 104 and a distal end 106, and membrane valve portion 150 extending radially outward from the main tubular body 102.

The sealing valve 100 is configured to be used in combination with a container (not shown as a whole) having an internal cavity 12, which should be hermetically sealed from the external environment 10 during normal operation thereof. The internal cavity 12 may be enclosed by a plurality of container walls, wherein at least one container wall 210 comprises at least one central bore 216, configured to receive the sealing valve 100. The container wall 210 may be any wall of the container, such as a top cover, a bottom base, or a sidewall. The container wall 210 can be either an integral stationary wall of the container, or a dynamically movable wall, such as a releasably attachable cover or a hinged pivotable cover.

The sealing valve 100 may be mounted against the central bore 216, such that the main tubular body 102 extends there-through and protrudes into the internal cavity 12 enclosed by the container. A sealing assembly 200 refers to a combination of a container wall 210 having at least one central bore 216, and at least one sealing valve 100 mounted within the corresponding central bore 216.

The terms "main body 102" and "main tubular body 102", as used herein, are interchangeable, and refer to a tubular structure defining an internal lumen in at least one state thereof. The term "tubular body" is meant to include a body having a circular, oval, elliptical, rectangular, square or any other cross-sectional shape. It will be understood that the main tubular body may assume a closed-end configuration in a specific state, but may transition between various states such that it will assume a configuration in which a lumen is defined between proximal and distal open ends in at least one state thereof.

The container wall 210 has a proximal wall surface 212, facing the external environment 10, and a distal wall surface 214, facing the internal cavity 12. The container wall 210 further comprises at least one central bore 216 extending through the proximal and distal wall surfaces 212 and 214, respectively. In some exemplary implementations, the container wall 210 comprises more than one central bore 216, such that a plurality of sealing valves 100 can be mounted within a respective plurality of central bores 216.

In some exemplary implementations, more than one container wall 210 comprises at least one central bore 216, each configured to accept a corresponding sealing valve 100.

In some implementations, the container wall 210 further comprises at least one peripheral opening 218 (see FIG. 3), offset radially outward from the central bore 216. In some implementations, a plurality of peripheral openings 218 may be disposed around the central bore 216.

The sealing valve 100 is configured to receive a tube 50 that may extend axially through its main body 102. The tube 50 can be a hollow tube, defining a tube inner lumen 52. In other implementations, the tube 50 may represent any other member insertable through the main body 102, with or without an inner lumen 52, such as a pipe, an electrode, a rod, and the like. Moreover, a tube 50 may be provided with a circular, oval, rectangular, or any other cross-sectional shape. The sealing valve 100 is configured to seal the tube 50 against the central bore 216, so as to prevent spontaneous gas or fluid flow between the external environment 10 and the internal cavity 12 through the central bore 216 and/or through the at least one peripheral opening 218. When the tube 50 is inserted through the sealing member 100, the distal end 106 is tightly pressed against the outer surface of the tube 50. In some implementations, the sealing assembly 200 further comprises the tube 50 extending through the sealing valve 100.

The term "proximal", as used herein, generally refers to the side or end of any device or a component of a device, which is closer to the external environment 10 and father from a center of the internal cavity 12.

The term "distal", as used herein, generally refers to the side or end of any device or a component of a device, which is closer to the center of the internal cavity 12 and father from the external environment 10.

The term "plurality", as used herein, means more than one.

The term "fluid", as used herein, refers to any of: liquid such as water or other aqueous or non-aqueous solutions, vapor, or gas.

The container wall 210 comprises a proximal wall surface 212 and a distal wall surface 214, wherein a wall thickness $t_w$ is defined between the proximal 212 and distal 214 wall surfaces. Each peripheral opening 218 extends through the entire wall thickness $t_w$.

In some exemplary configurations, the proximal end 104 defines a proximal opening 105 having an inner diameter $D_{pi}$, which is larger than the inner diameter $D_{di}$ of the opening defined by the distal end 106. The main body 102 comprises a tapering segment 110 disposed between the proximal end 104 and the distal end 106, which tapers radially inward in the distal direction. In some exemplary implementations, the tapering segment 110 may be angled so as to decrease in the distal direction from a diameter which is substantially equal to $D_{pi}$, to a diameter which is substantially equal to $D_{di}$.

The term "substantially", as used herein, modifies a particular value by referring to a range equal to the particular value, plus or minus ten percent (+/−10%). For example, a diameter which is substantially equal to a diameter value $D_{pi}$ is in the range of 90% to 110% of $D_{pi}$.

The tapering segment 110 may be shaped as a frustum as shown in FIGS. 1B and 2B, which may comprise a conical frustum or may comprise another form of frustum in other variations (e.g., pyramidal or another shape).

In some exemplary implementations, the main body 102 further comprises a proximal segment 108 extending distally from the proximal end 104, and may be provided with a uniform internal diameter which is substantially equal to $D_{pi}$. The proximal segment 108 can have a length $L_p$ that is at least equal to, or higher than, the thickness $t_w$.

In some exemplary implementations, the main body 102 further comprises a distal segment 112 extending proximally from the distal end 106 when a tube 50 is disposed within the sealing valve 100. The distal segment 112 may be provided, in some exemplary implementations, with a uniform internal diameter which is substantially equal to $D_{di}$. The length of the distal segment 112 can dictate the amount of surface contact between the sealing valve 100 and the tube 50.

The tapering segment 110 may extend, in some implementations, from the proximal segment 108 toward the distal end 106. The tapering segment 110 may extend, in some implementations, from the proximal segment 108 to the distal segment 112.

The proximal segment 108 has an outer diameter $D_{po}$ along at least a portion thereof, which is configured to face and/or contact the inner edges of the central bore 216. The proximal segment 108 can have a uniform outer diameter which is substantially equal to outer diameter $D_{po}$ along at least a portion of its length. At least a portion of the proximal segment 108 is configured to be sealingly pressed against the central bore 216, which in turn is provided with an internal bore diameter $D_b$.

In some implementations, the proximal segment 108 is configured to transition between a proximal free state, defined as a state in which the proximal portion is not disposed within the central bore 216 or any other circumferential boundary there-around, and a proximal mounted state, defined as a state in which at least a portion of the proximal segment 108 is situated within the central bore. In some exemplary implementations, the proximal segment 108 is sealed against the central bore 216 in the proximal mounted state.

In some exemplary implementations, the proximal segment 108 may be flexibly compressed in a radial direction. Specifically, the proximal segment 108 may be provided with an outer diameter $D_{po}$, which is substantially equal to, or slightly larger than, the internal bore diameter $D_b$ in the proximal free state, and is slightly compressed radially inward in the proximal mounted state such that $D_{po}$ is substantially equal to $D_b$, resulting in a portion of the proximal segment 108 tightly pressed against the central bore 216, which in turn results in a sealing effect therebetween.

The distal end 106 is radially expandable and may transition between several states, defined by the distal end inner diameter $D_{di}$. Specifically, when not subjected to flow-induced pressure gradient, the distal end 106 is configured to transition between a distal free state, defined as a state in which the distal end 106 is not disposed around a tube 50 extending there-through, as shown in FIG. 3, and a distal sealed state, defined as a state in which the distal end 106 circumscribes and is tightly pressed against the outer surface of a tube 50 extending there-through, as shown in FIG. 4.

In some exemplary implementations, the distal segment 112 is similarly configured to transition between the distal free-state, wherein no portion thereof is disposed around a tube 50 extending there-through, and the distal sealed state, in which at least a portion of the distal segment 112 circumscribes and is tightly pressed against the outer surface of a tube 50 extending there-through.

In some exemplary implementations, the distal end 106 may be provided with an inner diameter $D_{di}$ which is substantially equal to or smaller than the outer diameter of the tube 50 that may be accommodated therein, in the distal free-state. Thus, when the tube 50 is pushed through the sealing valve 100, the distal end 106 expands to tightly circumscribe the tube 50, resulting in a sealing effect there-between.

In some exemplary implementations, the distal segment 112 may be provided with a uniform inner diameter $D_{di}$ which is substantially equal to or smaller than the outer diameter of the tube 50 that may be accommodated therein, in the distal free-state. Thus, when the tube 50 is pushed through the sealing valve 100, the distal segment 112 expands to tightly circumscribe the tube 50, resulting in a sealing effect there-between.

In some exemplary implementations, the distal end 106 may define a distal edge 107 that can be flexibly expanded in a radial direction. The distal edge 107 may be formed as a circular planar edge configured to expand in a radial direction. In some exemplary implementations, the distal edge 107 may be provided with an inner diameter $D_{di}$ which is substantially equal to or smaller than the outer diameter of the tube 50 that may be accommodated therein, in the distal free-state. Thus, when the tube 50 is pushed through the sealing valve 100, the distal edge 107 expands to tightly circumscribe the tube 50, resulting in a sealing effect there-between.

In some implementation, the sealing valve further comprises a proximal flange 122 extending radially outward from the proximal end 104. The proximal flange 122 may be utilized to assist in positioning of the sealing valve 100 within the central bore 216. In some exemplary implementations, the proximal flange 122 extends radially outward from another region of the proximal segment 108, which may be distal to the proximal end 104 (exemplary implementations not shown).

In some configurations, the proximal flange 122 may rest over the proximal wall surface 212, thereby preventing spontaneous displacement of the sealing valve 100 in a distally oriented direction.

As shown in FIGS. 3 and 4, the wall 210 may further comprise at least one peripheral opening 218 extending there-through, radially spaced from the central bore 216. In some implementations, a plurality of peripheral openings 218 are circumferentially spaced apart around the central bore 216.

The membrane valve portion 150 extends around and radially away from a periphery of the main tubular body 102. The membrane valve portion 150 comprises a membrane body 152 defined between a membrane juncture 154, along which the membrane body 152 is attached to the main body 102, and a membrane lip 156. The membrane valve portion 150 is resiliently biased toward the proximal direction, and is configured to bend distally when flow-induced pressure gradient is applied thereto by fluid flowing in the distal direction.

The membrane valve portion 150 is configured to resiliently press against the container wall 210 when the sealing valve 100 is mounted within the central bore 216, in a peripheral sealed state—defined as a state in which the membrane valve portion 150 is not deflected or bent in a distal direction due to flow-induced pressure gradient across the membrane body 152.

In some exemplary implementations, the membrane valve portion 150 is in the form of an inverted umbrella valve, having the membrane body 152 arched from the membrane juncture 154 in the proximal direction, so as to bias the membrane lip 156 toward the container wall 210. Thus, the membrane valve portion 150 may be configured to resiliently press the membrane lip 156 against the container wall 210 in a peripheral sealed state. In such implementations, the membrane lip 156 serves as a sealing lip.

The membrane lip 156 defines a membrane valve diameter $D_m$ which extends beyond the peripheral openings 218 of the wall container 210, such that the membrane valve portion 150 is configured to prevent fluid flow from the internal cavity 12 to the external environment 10 there-through, and vice-versa, in the peripheral sealed state.

Membrane valve cavity 14 is defined between the container wall 212 and the membrane valve portion 150 in the peripheral sealed state, such that the external environment 10 is in fluid communication with the membrane valve cavity 14 through the at least one peripheral opening 218.

Central gap 16 is defined as the gap formed between the portion of the sealing valve 100 which is spaced away from the tube 50, and the tube 50. For example, the central gap 16 shown in FIG. 14, in a distal sealed state, includes the gap formed between the proximal segment 108 and the tube 50, which can be of constant diameter, and the gap formed between the tapering segment 110 and the tube 50, which can have a diameter that decreases in the distal direction.

Thus, when the sealing valve 100 is mounted within the central bore 216 such that the proximal end 104 and/or the proximal segment 108 is in the proximal mounted state, and the membrane valve portion 150 is in the peripheral sealed state, and when the tube 50 extends through the sealing valve 100 such that the distal end 106 and/or the distal segment 112 is in the distal sealed state, fluid is prevented from escaping the internal cavity 12 to the external environment 10 through the central bore 216 or the peripheral openings 218, and vice versa.

Figure 5A:
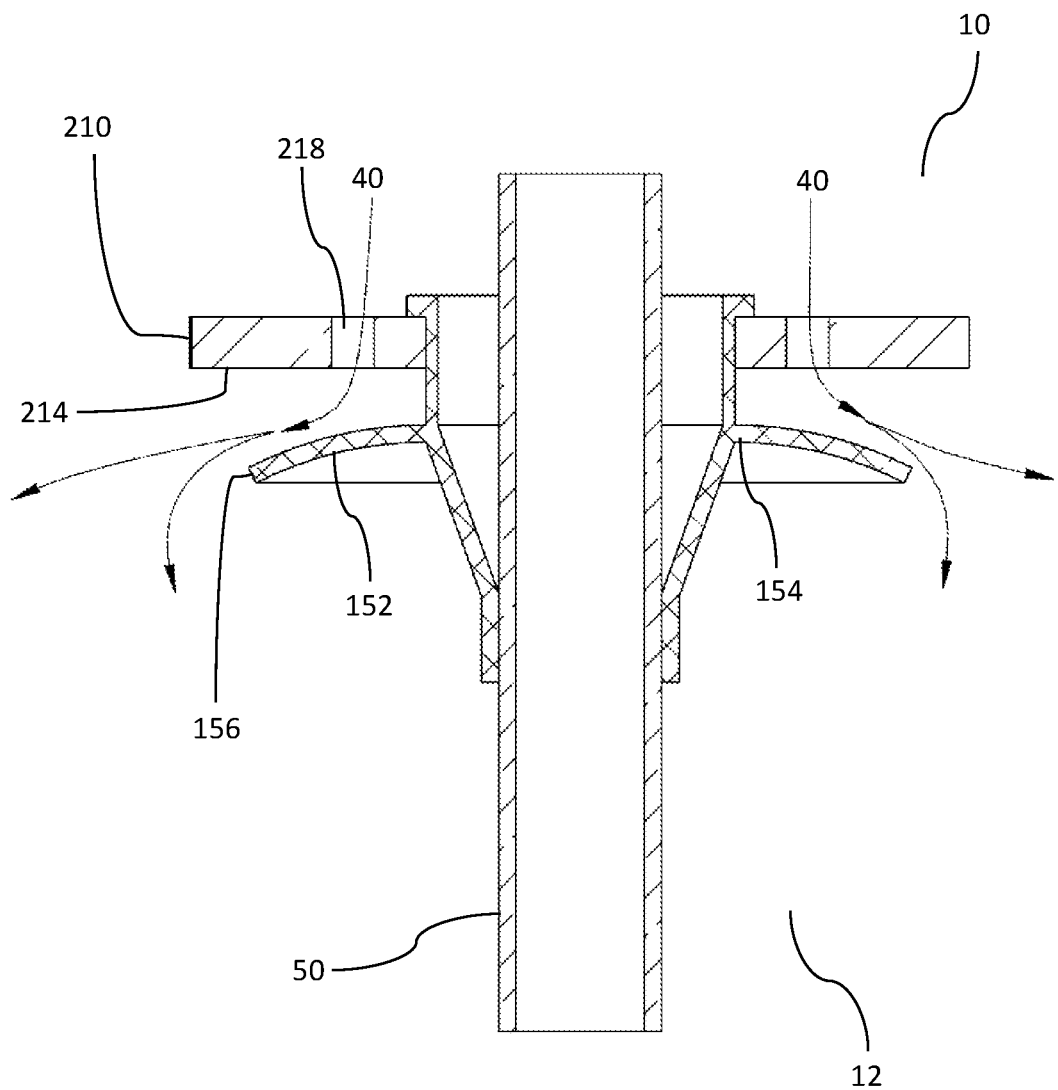
Figure 5B:
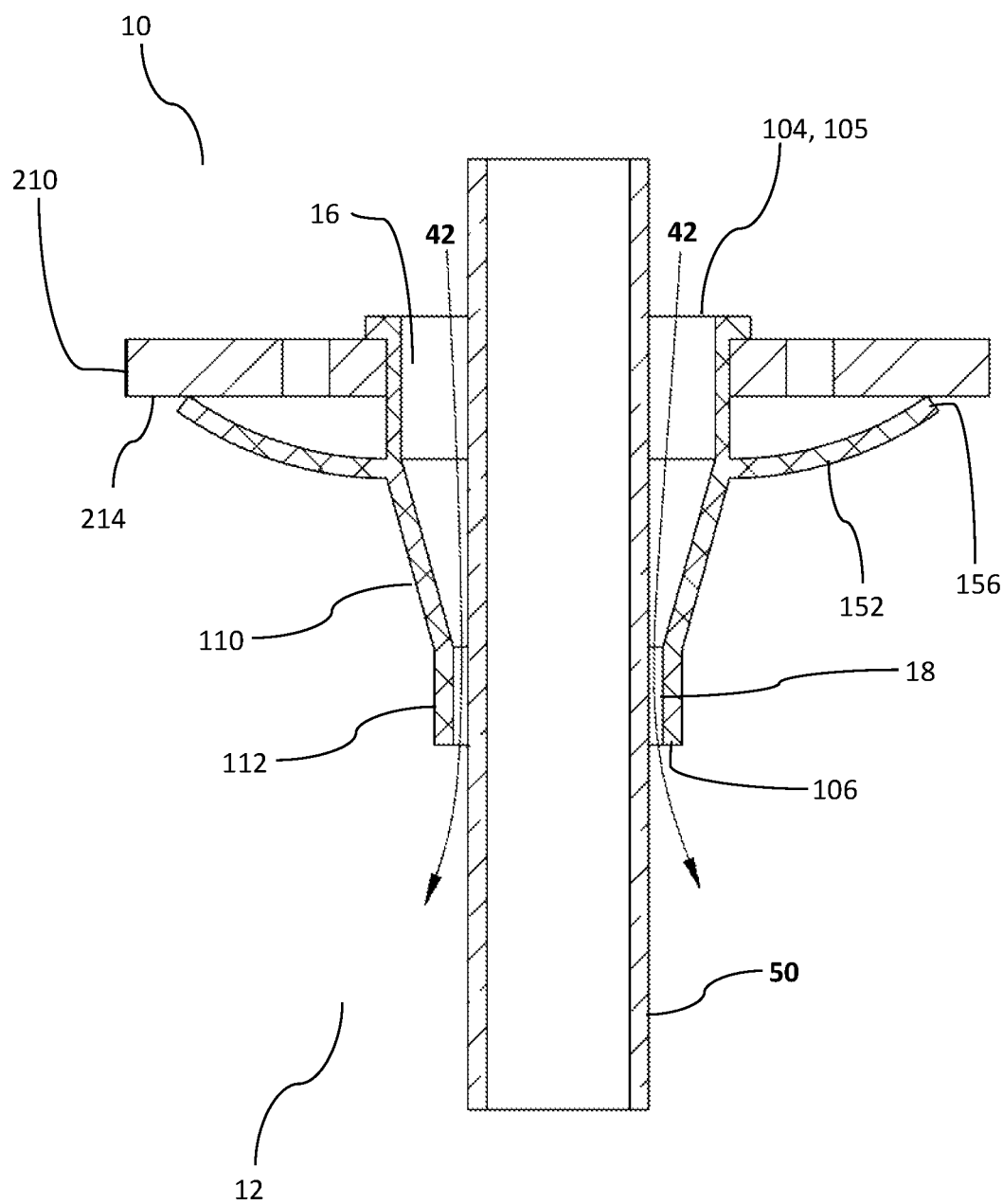
Figure 5C:
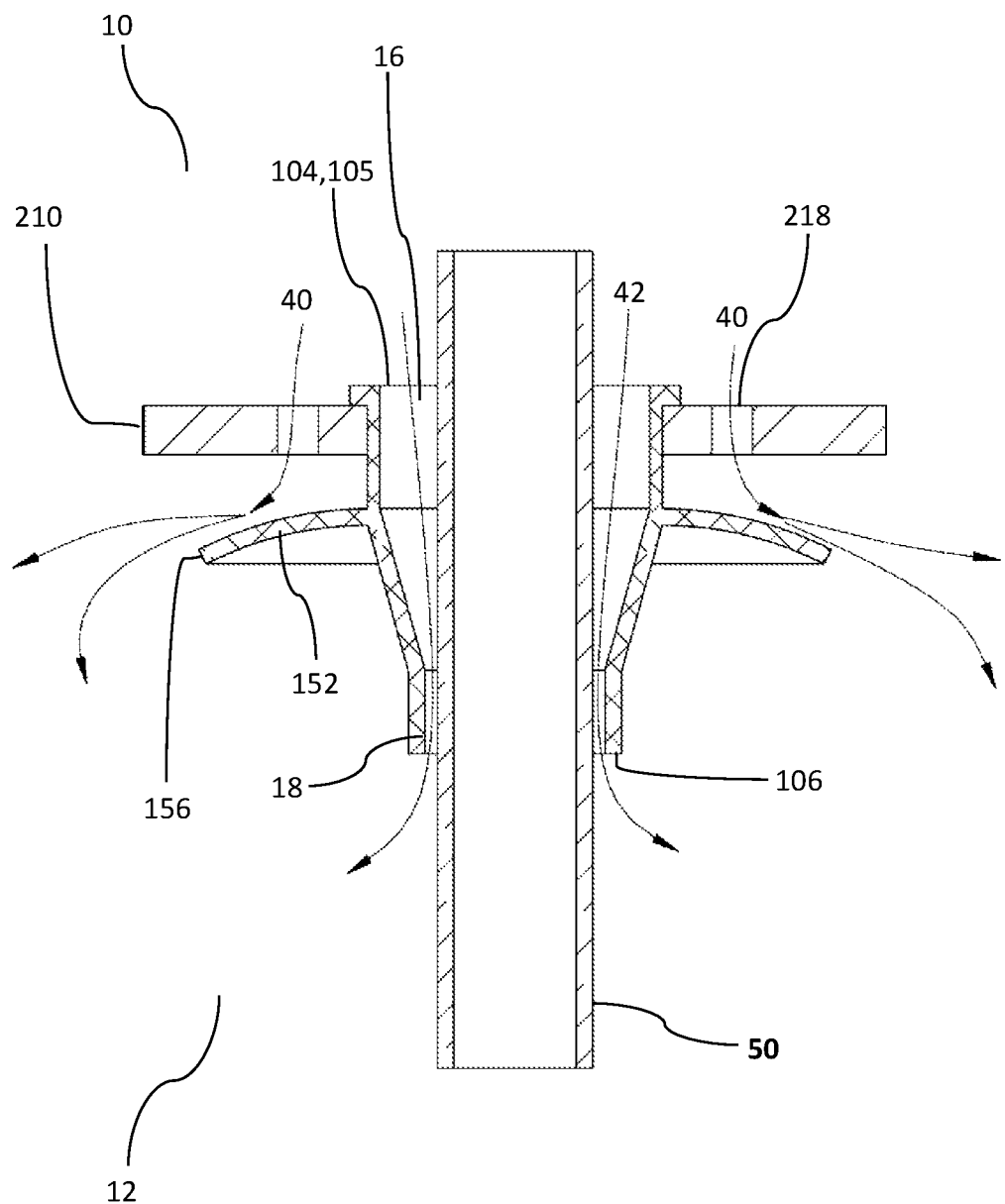

Reference is now made to FIGS. 5A-5C, showing an exemplary sealing assembly 200 with a sealing valve 100 in various states in which fluid may flow from the external environment 10 to the internal cavity 12 along various flow paths, namely an external or peripheral flow path, and an internal or central flow path.

The membrane valve portion 150 is movable between the peripheral sealed state, shown in FIG. 4, and the peripheral open state, shown in FIG. 5A. The membrane body 152 is made of a resilient flexible material, configured to deflect in a distal direction, distancing the membrane lip 156 away from the container wall 210, when fluid pressure is applied thereto, for example by fluid flowing through the peripheral openings 218 along a peripheral flow path 40 shown in FIG. 5A. The peripheral open state allows such fluid to flow around the bent or deflected membrane valve portion 150, into the internal cavity.

In some systems, such as closed bioreactors, the internal cavity needs to be kept hermetically sealed from the outer environment during an operational stage thereof so as to prevent contamination of the bio-organisms kept therein. Such system may be required to allow occasional delivery of fluids, such as cleaning solutions, into the internal cavity, for periodical sterilization procedures. Sealing valves 100 according to the current disclosure may be used to seal the internal cavity 12 from the external environment 10 during normal operation of such systems, and to allow occasional flow of fluids into the internal cavity 12, for example through peripheral openings 218, biasing the membrane valve portion 150 to the peripheral open state, for example during periodical sterilization procedures.

As shown in FIG. 5A, when fluid, flowing through the at least one peripheral opening 218, exerts a force sufficient to deflect the membrane valve portion 150 to the peripheral open state, the membrane valve portion 150 allows for fluid to propagate in the direction of arrows 40 into the internal cavity 12. When force is no longer applied to the membrane body 152, for example—as no more fluid is ejected through peripheral openings 218, the resilient nature of the membrane valve portion 150 will resist flexing and revert back to the peripheral sealed state shown in FIG. 4, to inhibit the transmission of moisture, fluids, dust, dirt, debris, etc. through the peripheral openings 218.

In some instances, debris may accumulate in the central gap, between the main body 102 and the tube 50 in the distal sealed state. While cleaning solution flowing around the membrane valve portion 150 in the peripheral open state, may serve to clean at least portions of the outer surfaces of the sealing valve, it may be desirable to enable cleaning functionality of the inner surfaces of the main tubular body 102 as well.

The distal end 106 is movable between the distal sealed state, shown in FIG. 4, and the distal open state, shown in FIG. 5B. The distal end 106 is made of a resilient flexible material, configured to expand in a radial direction, distancing away from the container tube 50, when fluid pressure is applied thereto, for example by fluid flowing distally from the proximal opening 105 through the central gap 16 along a central flow path 42 shown in FIG. 5B. The distal open state allows such fluid to flow through the expanded distal end 106, into the internal cavity 12, washing debris accumulated in the central gap 16, or smeared along the internal surfaces of the main tubular body 102 and/or the external surface of the tube 50 there-along.

In some instances, it may be desirable to separately inject fluid, such as cleaning liquids, either through peripheral openings 218, as shown in FIG. 5A, or through the proximal opening 105, as shown in FIG. 5B. In some instances, such as during sanitization procedures of bio-reactor systems, it may be desirable to inject fluids, such as cleaning liquids, through the peripheral openings 218 and the proximal opening 105, simultaneously, as shown in FIG. 5C. This may serve the purpose of simultaneous cleaning of the internal cavity 12 as well as both sides, i.e., internal and external, of the sealing valve 100, at the same time.

Advantageously, the structural configuration of the sealing valve 100 enables fluid flow in the same distal direction, flowing along both the external and internal surfaces of the sealing valve 100 to enable such surfaces to be periodically washed, for example by cleaning solutions, while the sealing valve 100 remains mounted within the container wall 210. Elimination of the requirement to remove the sealing valve 100 from the container wall 210 for periodic cleaning thereof, followed by reattachment thereof, may save maintenance costs by reducing time and efforts dedicated to such procedures.

In some exemplary implementations, the distal edge 107 is movable between the distal sealed state and the distal open state. The distal edge 107 is configured to expand in a radial direction, distancing away from the container tube 50, when fluid pressure is applied thereto, for example by fluid flowing from the opening at the proximal end 104 through the central gap 16 along a flow path 42 shown in FIG. 5B. The distal open state allows such fluid to flow through the expanded distal edge 107, into the internal cavity, washing debris accumulated in the central gap 16, or smeared along the internal surfaces of the main body 102 and/or the external surface of the tube 50 there-along.

In some exemplary implementations, the distal segment 112 is movable between the distal sealed state and the distal open state. The distal segment 112 is made of a resilient material, configured to expand in a radial direction, distancing away from the container tube 50, when fluid pressure is applied thereto, for example by fluid flowing from the opening at the proximal end 104 through the central gap 16 along a flow path 42 shown in FIG. 5B. The distal open state allows such fluid to flow through the expanded distal segment 112, into the internal cavity, washing debris accumulated in the central gap 16, or smeared along the internal surfaces of the main body 102 and/or the external surface of the tube 50 there-along.

As shown in FIG. 5B or 5C, when fluid, flowing through the proximal opening 105, exerts a force sufficient to radially expand the distal end 106 and/or the distal edge 107 and/or the distal segment 112, to the distal open state, fluid is allowed to propagate in the direction of arrows 42 through the central gap 16 and into the internal cavity 12. When force is no longer applied to the distal end 106 and/or the distal edge 107 and/or the distal segment 112, for example—as no more fluid is injected through the opening defined by the proximal end 104, the resilient nature of the distal end 106 and/or the distal segment 112 will resist flexing and revert back to the distal sealed state shown in FIG. 4, to inhibit the transmission of moisture, fluids, dust, dirt, debris, etc. through the central gap 16.

The sealing valve 100 may comprise elastomeric materials, configured to provide material resiliency and sufficient flexibility to transition between the different states of the valve disclosed herein above. It may be appreciated that the entire sealing valve 100, according to any of the implementations disclosed herein, may be formed as a monolithic structure, such as a single piece molded or otherwise manufactured structure, to reduce manufacturing costs.

Figure 7:
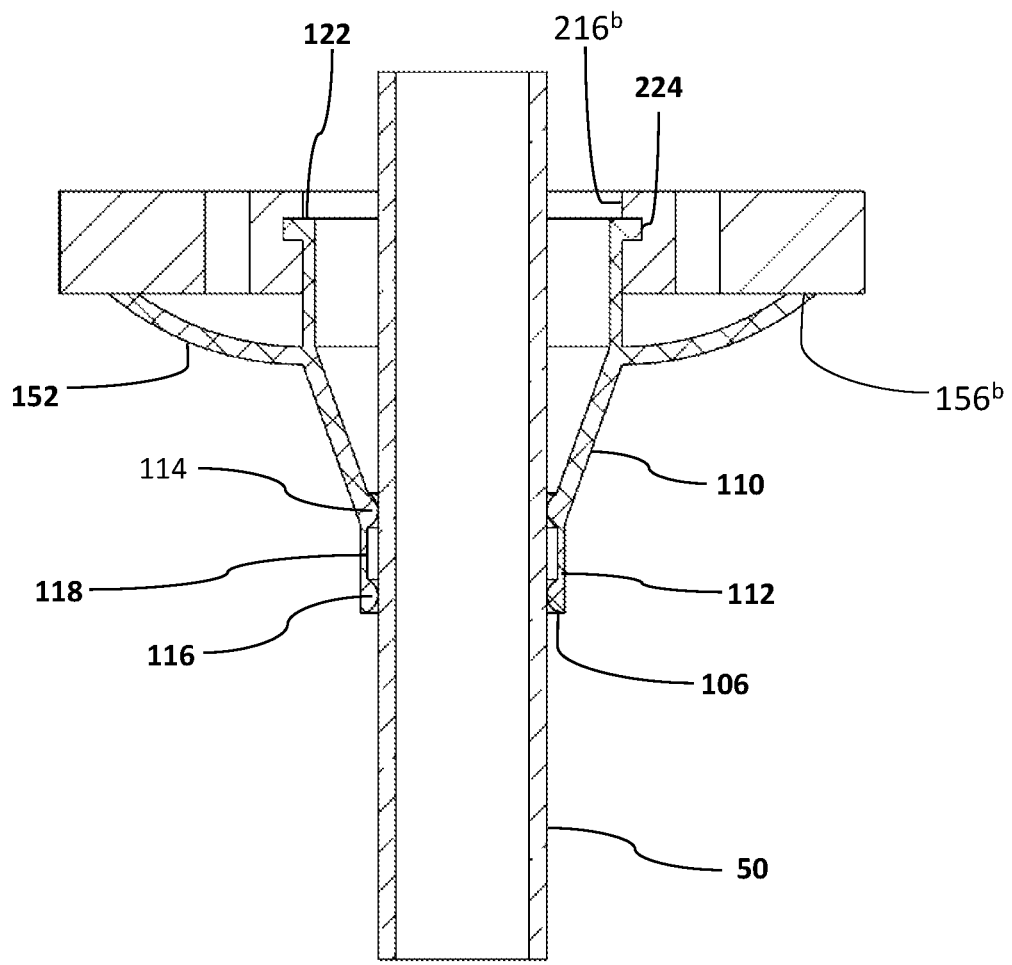

Reference is now made to FIGS. 6-10, showing exemplary alternative implementations of some components of the sealing valve 100 and/or the container wall 210. FIG. 6 shows a perspective view of a sealing valve 100 provided with a flat membrane lip 156$^b$, according to some implementations. FIG. 7 shows a cross-sectional view of the sealing valve 100 of FIG. 6 mounted within a container wall 210 having a bore groove 224, according to some implementations. FIG. 8 shows a cross-sectional view of the sealing valve 100 of FIG. 6 mounted within a container wall 210 having a bore recess 222, according to some implementations. FIG. 9 shows a cross-sectional view of a sealing assembly 200, which includes a sealing valve 100 provided with a rounded membrane lip 156$^c$, according to some implementations. FIG. 10 shows a cross-sectional view of a sealing assembly 200, including a sealing valve 100 devoid of an annular distal segment, mounted within a container wall 210 having a receiving channel 264, according to some implementations.

In some exemplary implementations, the membrane lip 156 may be provided as an orthogonally cut membrane lip 156$^a$, shown for example in FIG. 3. An orthogonally cut membrane lip 156$^a$ is provided with a straight profile that is substantially perpendicular to the orientation of the membrane body 152 in the vicinity of the membrane lip 156$^a$. In such implementations, as shown in FIG. 3, a proximal corner of the orthogonally cut membrane lip 156$^a$ may be pressed against the container wall 210 in the peripheral sealed state.

In some exemplary implementations, the membrane lip 156 may be provided as a flat membrane lip 156$^b$, shown for example in FIGS. 6 and 7. A flat membrane lip 156$^b$ is provided with a straight profile that is substantially parallel to the proximal wall surface 212. Such implementations may be preferable over orthogonally cut membrane lips 156$^a$, providing a larger contact area against the container wall 210 in the peripheral sealed state.

In some exemplary implementations, the membrane lip 156 may be provided as a rounded membrane lip 156, shown for example in FIG. 9. Such implementations may be preferable over flat membrane lip 156$^b$, as flat membrane lips 156$^b$ provide a maximal contact area against the container wall only within a small range of membrane valve diameters $D_m$ in the peripheral sealed state, while rounded profiles may enable a higher flexibility providing a comparable contact area along a wide range of potential membrane valve diameters $D_m$ in the peripheral sealed state. This higher flexibility may allow the sealing valve 100 to be mounted within various types of container walls 210, for example—provided with various magnitudes of wall thickness $t_w$, while still providing the desire seal there-against.

The term "flat", as used herein, refers to a surface that is without significant projections or depressions.

In some exemplary implementations, container wall 210 comprises a flat distal wall surface 214$^a$, provided with a uniform flat surface at the region configured to contact the membrane lip 156, for example—between the peripheral opening 218 and radially away from the point of contact with the membrane lip 156, as shown in FIG. 9.

In some exemplary implementations, container wall 210 comprises a distal wall surface 214$^b$, having a receiving channel 264, which can be an annular channel, formed radially away from the peripheral opening 218 as shown in FIG. 10. The receiving channel 264 is positioned at a position designated to receive the membrane lip 156, for example spanning a range that includes the membrane valve diameter $D_m$. The receiving channel 264 is dimensioned to receive and accommodate the membrane lip 156 in the peripheral sealed state, advantageously configured to prevent the membrane lip 156 from spontaneously slipping in the radial direction between the radial boundaries of the receiving channel 264. The receiving channel may be provided with a width that is larger than the thickness of the membrane valve portion 150, to enable simple placement of the membrane lip 156 therein.

In some exemplary implementations, the central bore 216 may comprise a bore groove 224, which can be an annular groove, as shown in FIG. 7. The bore groove 224 is disposed along the inner periphery of the central bore 216, spaced away from both the proximal wall surface 212 and the distal wall surface 214, configured to accommodate the proximal flange 122. The bore groove 224 can be dimensioned to match the dimensions of the proximal flange 122. Advantageously, such implementations may enhance the retaining engagement of the sealing valve 100 within the container wall 210. The proximal flange 122 may be situated within the bore groove 224 by temporarily squeezing the proximal end 104 and/or the proximal segment 108 radially inward to push it axially through the central bore 216, until the proximal flange 122 is positioned against the bore groove 224, allowing it to resiliently spring back radially outward into the bore groove 224.

The terms "radially inward" or "radially outward", refer to a direction or position which is closer, or away from, respectively, a centerline 70 (see FIG. 8) of the sealing valve 100. In some implementations, the sealing valve 100 is coaxial with the central bore 216 and/or the tube 50, all sharing a common centerline 70.

The term "longitudinal" refers to a direction, orientation, or measurement that is parallel to the longitudinal centerline 70.

In some exemplary implementations, the central bore 216 may comprise a bore recess 222, which can be an annular recess, as shown in FIG. 8. The bore recess 222 is disposed along the inner periphery of the central bore 216, spaced away from the distal wall surface 214 and open ended along the proximal wall surface 212. The bore recess 222 defines an annular shoulder around the proximal end of the central bore 216 configured to accommodate the proximal flange 122. The bore recess 222 can be dimensioned to match the dimensions of the proximal flange 122. Advantageously, such implementations may enhance the retaining engagement of the sealing valve 100 within the container wall 210, while simplifying the process of accommodating the proximal flange 122 therein. The proximal flange 122 may be situated within the bore recess 222 by situating it over the recess from a proximal direction. The height of the bore recess 222 can be substantially equal to that of the proximal flange 122, such that the proximal flange 122 is flush with the proximal wall surface 212 when situated within the bore recess 222.

As mentioned above for some exemplary implementations, the main body 102 may comprise a tubular distal segment 112, provided with a uniform inner diameter along its length, between the distal end 106 and the transition to the tapering segment 110, as shown for example in FIGS. 1A to 5C.

In some exemplary implementations, the main body 102 comprises a distal segment 112 having a distal groove 118, which can be an annular groove, as shown in FIGS. 7 and 8. A first distal lip 114 is formed between the groove 118 and the tapering segment 110. A second distal lip 116 is formed between the groove 118 and the distal end 106. As shown, a closed annular channel may be formed between the groove 118 and the tube 50, while the first and second distal lips 114 and 116, respectively, are tightly pressed against the outer surface of the tube 50 in the distal sealed state.

In some exemplary implementations, the main body 102 is devoid of a longitudinally extending distal segment 112, such that the distal end 106 and the distal edge 107 defined thereby, are defined along a distal end of the tapering segment 110, as shown in FIG. 10.

Reference is now made to FIGS. 11A-13C, showing various exemplary implementations of sealing valve 100 provided with distal flaps 120 in a distal free state, in some implementations. FIGS. 11A-11B show perspective views of a sealing valve 100 provided with distal flaps 120 from a top-side and a down-side view angle, respectively, in a distal free state thereof, according to some implementations. FIG. 11C shows a distal elevation view of the sealing valve 100 of FIGS. 11A-11B. FIG. 11D shows a perspective view of the sealing valve 100 of FIGS. 11A-11C in a distal sealed or open state. FIGS. 12A and 12B shows a perspective view and a side view of a sealing assembly 200, which includes the sealing valve 100 of FIGS. 11A-11D mounted within a container wall 210 in a distal sealed state. FIGS. 13A-13B show perspective views of a sealing valve 100 provided with distal flaps 120 from a top-side and a down-side view angle, respectively, according to some alternative implementations. FIG. 13C shows a side view of the sealing valve 100 of FIG. 13A-13B.

According to some implementations, the distal segment 112 may comprise a plurality of flaps 120 extending from and attached to the tapering segment 110, wherein the flaps 120 are biased toward each other in the distal free-state, and are pivotable about the edge attached to the tapering segment 110. The flaps 120 can be integrally formed with the tapering segment 110, and may include a living hinge at the transition to the tapering segment 110.

According to some exemplary implementations, the sealing valve 100 comprises a distal segment 112$^b$ having a plurality of flaps 120$^b$, resiliently biased radially inward toward each other, together forming a flat surface which is substantially orthogonal to the central axis of the main body 102 in the distal free state, as shown in FIGS. 11A-11C. In such implementations, the longitudinal length of the distal segment 112$^b$ in the distal free-state can be equal to the thickness of the flaps 120$^b$.

A tube 50 may be pushed distally through the main body 102, so as to push the flaps 120$^b$ sideways to the distal sealed state, shown in FIGS. 12A-12B. FIG. 11D shows the flaps 120$^b$ extended away from each other along the distal end 106$^b$, which can be representative of either the distal sealed state shown in FIGS. 12A-12B if the flaps 120$^b$ are tightly pressed against the tube 50, or a distal open state if the flaps 120$^b$ expand further radially away from the tube 50, for example during fluid flowing in direction 42 as described in conjunction with FIGS. 5B-5C. As shown, the distal edge 107$^b$ follows a zig-zagged pattern along the flaps 120$^b$ in a distal sealed state or a distal open state.

According to some exemplary implementations, the sealing valve 100 comprises a distal segment 112$^c$ having a plurality of flaps 120$^c$ configured to bias toward each other, together forming a conical or pyramid-shaped geometry, pointing distally in the distal free state, as shown in FIGS. 13A-13C. The flaps 120$^c$ of the distal segment 112$^c$ may otherwise function in the same manner described for the flaps 120$^b$ of the distal segment 112$^b$ above. While flat and conical or pyramid-shaped configurations are shown for distal segments 112 equipped with flaps 120, it will be clear that other shapes are contemplated, such as frustoconical or dome-shaped geometries, formed by the flaps 120 in the distal free-state.

Reference is now made to FIGS. 14A-17, showing exemplary alternative implementations of the container wall 210. FIGS. 14A and 14B shows a perspective view and a partial cutaway view in perspective of sealing assembly 200, wherein the container wall 210 comprises a hollow extension, according to some implementations. FIG. 15 shows a partial cutaway view in perspective of a sealing assembly 200, wherein the container wall 210 comprises a peripheral inlet chamber 244, according to some implementations. FIG. 16 shows a partial cutaway view in perspective of a sealing assembly 200, wherein the container wall 210 comprises a peripheral inlet chamber 244$^b$, according to some alternative implementations. FIG. 17 shows a partial cutaway view in perspective of sealing assembly 200, wherein a plurality of sealing valves 100 are mounted within a container wall 210 provided with a peripheral inlet chamber 244$^c$ and a central inlet chamber 254, according to some implementations.

According to some exemplary implementations, the at least one peripheral opening 218 is circular of elliptic. The at least one peripheral opening can include, in some implementations, a plurality of peripheral openings 218, which may be equally circumferentially spaced from each other around the central bore 216, or can be spaced at varying distanced from each other. FIG. 14A shows an exemplary configuration of four circularly shaped peripheral openings 218, equi-spaced from each other such that each peripheral opening 218 is equally distanced from the central bore 216, and each couple of peripheral openings 218 are equally spaced from each other.

In some exemplary implementations, the at least one peripheral opening 218 is in the form of an elongated slot, such as an arcuate or circular slot. FIGS. 16 and 17 show exemplary configurations of four arcuate slot-shaped peripheral openings 218, disposed around the central bore 216, forming radial ribs 220 between each couple of adjacent peripheral openings 218.

While circular or slot-shaped peripheral opening 218 are shown in FIGS. 14A-18, it will be clear than any other shape, such as oval openings, triangular openings, and the like, is contemplated. Moreover, while the illustrated examples show configurations of similarly shaped peripheral opening 218, it will be clear that a container wall 210 can include a plurality of differently-shaped opening.

In some cases, the distal segment 112 serves to retain the tube 50 in position, preventing it from slipping axially in a distal sealed state due to friction exerted by the distal segment 112 on the tube 50. However, as the distal segment expands radially away from the tube 50 in the distal open state, such as shown, for example, in FIGS. 5B-5C, the tube may slip through the central opening of the main body 102, in the absence of any other retaining means.

According to some exemplary implementations, the container wall 210 further comprises a hollow extension 226, extending proximally from the proximal wall surface 212 around the central bore 216, as shown in FIGS. 14A-14B. The inner diameter of the hollow extension 226 can be equal to the bore diameter $D_b$. In some implementations, the length of the hollow extension is higher than the wall thickness $t_w$. In some exemplary implementations, the hollow extension 226 is situated between the central bore 216 and the peripheral openings 218.

It will be clear that referral to "peripheral openings 218", as used herein, without specifically referring to "a plurality of peripheral openings 218", may be used interchangeably with the term "at least one peripheral opening 218", and may thereby include also a single peripheral opening 218.

The hollow extension 226 can include an extension threading 232 along its outer proximal surface. The container wall 210 can further include a separable cap 236 provided with a cap distal opening 238 and a cap threading 240 along its inner distal surface, matching the extension threading 232. Thus, the cap 236 may be threadedly engaged with the hollow extension 226. The diameter of the cap distal opening 238 can be equal to the inner diameter of the hollow extension 226.

As further shown in FIG. 14B, a gasket 60, such as an O-ring, can be retained between the hollow extension 226 and the cap 236. When the gasket 60 is firmly pressed between the hollow extension 226 and the cap 236, it may protrude radially inward so as to press against the tube 50. The gasket 60 may formed from a squeezable material, such that when axial force is applied thereto, as the cap 236 is further threaded around the hollow extension 226, it is squeezed so as to further protrude radially inward and apply pressure against the tube 50. The pressure applied by the gasket 60 against the tube 50 is preferably sufficient to retain the tube 50 in position during the distal open state of the sealing valve 100.

In some exemplary implementations, the hollow extension 226 comprises an extension proximal recess 234, configured to serve as a seat for accommodating the gasket 60. In some exemplary implementations, the cap 236 further comprises a cap recess 242 around the cap distal opening 238, configured to be placed over the gasket 60.

In some implementations, the cap 236 may be hollow, such that the cap distal opening 238 extends along its length as shown in FIGS. 14A-14B. In alternative implementations, the cap 236 may be cup-shaped, having a close-ended proximal end (implementations not shown).

The terms "cap 236" and "separable cap 236", as used herein, are interchangeable.

The inner diameter of the hollow extension 226 is preferably designed to be larger than the outer diameter of the tube 50 that may extend there-through, so that a gap formed between the hollow extension 226 and the tube 50 may allow fluids, such as cleaning liquids, to flow there-through toward the central bore 216 and the central gap 16.

While the exemplary illustration show embodiments of a cap 236 having a cap distal opening 238 with an internal cap threading 240, which can be threaded with an external extension threading 232, other implementations may include a cap provided with an external cap threading, which can be threaded with an internal extension threading (implementations not shown). In such implementations, the diameter of the cap, at least along the cap threading, can be similar to the internal diameter of the hollow extension 226, and the cap can be provided as a full-matter component, i.e. devoid of a cap distal opening.

In some exemplary implementations, the hollow extension 226 further comprises at least one extension inlet opening 228 in fluid communication with the internal space of the hollow extension 226. An extension inlet port 230 may extend radially outward from the extension inlet opening 228. The extension inlet port 230 may serve as a fitting for a hose or any other liquid directing means that may be attached thereto, to direct fluids, such as cleaning liquids, through the extension inlet opening 228 toward the central bore 216. While the extension inlet port 230 is illustrated in FIGS. 14A-14B oriented perpendicularly to the outer surface of the hollow extension 226, it will be clear that other orientations, such as angled orientations, are contemplated.

In use, fluid may be directed through the extension inlet port 230 and the extension inlet opening 228 into the gap formed between the hollow extension 226 and the tube 50. The fluid may further flow in a distal direction toward the central bore 216 and into the central gap 16, so as to expand the distal end 106 of the sealing valve 100 to the distal open state, flowing onward into the internal cavity 12.

In some exemplary implementations, the container wall 210 further comprises a peripheral inlet chamber 244 extending proximally from the proximal wall surface 212, and sealingly attached to at least one hollow extension 226, as shown in FIG. 15. The inlet chamber 244 comprises at least one peripheral chamber sidewall 248 extending proximally from the proximal wall surface 212, and a peripheral chamber proximal wall 246 extending between the at least one peripheral chamber sidewall 248 and the hollow extension 226. The peripheral chamber proximal wall 246 may be parallel with the proximal wall surface 212 as shown in FIG. 15, or it may be angled relative thereto (angled orientation not shown).

The at least one peripheral chamber sidewall 248 is disposed radially away from the at least one peripheral opening 218. Thus, the peripheral inlet chamber 244 defines encloses a peripheral chamber inner space 20, defined between a portion of the proximal wall surface 212 that includes the at least one peripheral opening 218, the at least one peripheral chamber sidewall 248, the peripheral chamber proximal wall 246, and the hollow extension 226.

In some implementations, the peripheral inlet chamber 244 comprises a single continuous peripheral chamber sidewall 248, to define a ring-shaped peripheral chamber inner space 20 as illustrated in FIG. 15. In alternative implementations, the peripheral inlet chamber 244 can include a plurality of peripheral chamber sidewalls 248, such as four peripheral chamber sidewalls $248^c$ that may enclose a rectangular peripheral chamber inner space 20 as illustrated in FIG. 17.

In some exemplary implementations, the peripheral inlet chamber 244 further comprises at least one peripheral chamber opening 250 in fluid communication with the peripheral chamber inner space 20. A peripheral chamber port 252 may extend from the peripheral chamber opening 250. The peripheral chamber port 252 may serve as a fitting for a hose or any other liquid directing means that may be attached thereto, to direct fluids, such as cleaning liquids, through the peripheral chamber port 252 toward the peripheral chamber opening 250. While the peripheral chamber opening 250 is shown in FIG. 15 comprised in the peripheral chamber proximal wall 246, such that the peripheral chamber port 252 extends proximally therefrom, it will be clear that a peripheral chamber opening 250 may be similarly comprised within the at least one peripheral chamber sidewall 248, as shown for example in FIG. 17, such that the peripheral chamber port 252 may extend radially away therefrom.

In some exemplary implementations, as illustrated in FIG. 15, the peripheral chamber proximal wall 246 is distal to the extension inlet opening 228. In use, fluid may be directed through the peripheral chamber port 252 and the peripheral chamber opening 250 into the peripheral chamber inner space 20. Since the peripheral chamber inner space 20 is in fluid communication with the peripheral openings 218, the fluid may further flow in a distal direction through the peripheral openings 218, for example into the membrane valve cavity 14, so as to deflect the membrane valve portion 150 to the peripheral open state, allowing the fluid to flow onward into the internal cavity 12.

FIG. 16 shows another exemplary implementation of a peripheral inlet chamber $244^b$, which may be identical to peripheral inlet chamber 244, described and illustrated in conjunction with FIG. 15, except that the peripheral chamber proximal wall $246^b$ is proximal to the extension inlet opening 228, such that the peripheral chamber inner space 20 is in fluid communication with the extension inlet opening 228 as well. In such implementations, fluid may be directed through the peripheral chamber port $252^b$ and the peripheral chamber opening $250^b$ into the peripheral chamber inner space $20^b$. The fluid may flow from the peripheral chamber inner space $20^b$ concurrently through the extension inlet opening 228 toward the central bore 216, and through the peripheral openings 218, so as to flow along both sides of the sealing valve 100 as described and illustrated in conjunction with FIG. 5C.

Preferably, the extension threading 232, to which the cap 236 may be screwed, is positioned proximal to the peripheral chamber proximal wall 246 to enable convenient attachment or release of the cap 236 to and from the hollow extension, respectively.

While the peripheral inlet chambers 244 and 244$^b$ illustrated in FIGS. 15 and 16, respectively, encompass a single hollow extension 226 extending there-through, in some exemplary implementations, a single inlet chamber 244 may encompass a plurality of hollow extensions 226. FIG. 17 shows a peripheral inlet chambers 244$^c$, which may be similar to the peripheral inlet chambers 244 described and illustrated in FIG. 15, except that it is box-shaped around a plurality of hollow extensions 226. While four hollow extensions 226 are shown to extend through the peripheral inlet chambers 244$^c$ in FIG. 17, it will be clear than any other number of hollow extensions 226 is contemplated.

The peripheral inlet chamber 244$^c$ comprises peripheral chamber sidewalls 248$^c$ extending proximally from the proximal wall surface 212, positioned radially away from all of the peripheral openings 218 circumscribing the central bore 216 encompassed by the peripheral inlet chamber 244$^c$. The peripheral inlet chamber 244$^c$ further comprises a peripheral chamber proximal wall 246$^c$ extending between the peripheral chamber sidewalls 248$^c$ and the plurality of hollow extensions 226, positioned distal to the extension inlet ports 230. Thus, the peripheral chamber inner space 20$^c$ is defined between a portion of the proximal wall surface 212 that includes the peripheral openings 218 surrounding the plurality of central bores 216, the peripheral chamber sidewalls 248$^c$, the peripheral chamber proximal wall 246$^c$, and the plurality of hollow extensions 226.

As further shown in the exemplary illustrated implementation, at least one peripheral chamber sidewall 248$^c$ comprises at least one peripheral side opening 250$^c$ with a peripheral chamber port 252 extending therefrom.

In some exemplary implementations, the container wall 210 further comprises a central inlet chamber 254, proximal to the peripheral inlet chamber 244. The central inlet chamber 254 comprises at least one central chamber sidewall 258, extending proximal to the peripheral chamber proximal wall 246, and a central chamber proximal wall 256 extending between the at least one central chamber sidewall 258 and the at least one hollow extension 226 extending therethrough, positioned proximal to the respective at least one extension inlet opening 228.

FIG. 17 shows an exemplary central inlet chamber 254 comprising a plurality of central chamber sidewalls 258 extending proximally from the peripheral chamber proximal wall 246$^c$, potentially in alignment with the peripheral chamber sidewalls 248$^c$. Preferably, the same hollow extensions 226, such as the four hollow extensions 226 illustrated in FIG. 17, extend through both the peripheral inlet chamber 244 and the central inlet chamber 254.

The central chamber inner space 22 is defined between the peripheral chamber proximal wall 246, the central chamber sidewalls 258, the central chamber proximal wall 256, and the plurality of hollow extensions 226. The central inlet chamber 254 further comprises at least one central chamber opening 260 in fluid communication with the central chamber inner space 22. A central chamber port 262 may extend from the central chamber opening 260. The central chamber port 262 may serve as a fitting for a hose or any other liquid directing means that may be attached thereto, to direct fluids, such as cleaning liquids, through the central chamber port 262 toward the central chamber opening 260. While the central chamber opening 260 is shown in FIG. 17 comprised in a central chamber sidewall 258, such that the central chamber port 262 extends radially away therefrom, it will be clear that a central chamber opening 260 may be similarly comprised within the central chamber proximal wall 256, such that the central chamber port 262 may extend proximally therefrom.

While the various exemplary implementations illustrated in FIGS. 15-17 show peripheral chamber ports 252 or central chamber ports 262 oriented substantially perpendicular to the surface they extend from, such as a peripheral chamber proximal wall 246, a peripheral chamber sidewall 248, a central chamber proximal wall 256, and/or a central chamber sidewall 258, it will be clear that any peripheral chamber port 252 or central chamber port 262 may be angled relative to the surface it extends from (angled orientations not shown).

While the central chamber sidewalls 258 are illustrated in FIG. 17 in as continuously aligned with the peripheral chamber sidewalls 248, it will be clear that in alternative implementations, the central chamber sidewalls 258 may extend from the peripheral chamber proximal wall 246 at positions which are closer to the hollow extensions 226, since the central chamber sidewalls 258 are not required to be positioned away from the boundaries of peripheral opening 218. Moreover, the amount and shape of the at least one central chamber sidewall 258 does not have to be equal to that of the at least one peripheral chamber sidewall 248, such that the resulting shape of the central inlet chamber 254 does not have to be similar to that of the peripheral inlet chamber 244.

While the central inlet chamber 254 is illustrated as a box-shaped chamber having a four central chamber sidewalls 258, it will be clear that other shapes are contemplated. For example, the central inlet chamber 254 may include a single continuous central chamber sidewall 258, to define a ring-shaped central chamber inner space 22 similar to the shape of the peripheral chamber inner space 20 illustrated in FIG. 15.

While the central chamber sidewalls 258 are illustrated in FIG. 17 extending from the peripheral chamber proximal wall 246$^c$, in alternative implementations the central chamber sidewalls 258 may extend proximally from the proximal wall surface 212 at positions that are offset radially away from the peripheral chamber sidewalls 248 (exemplary implementations not shown). In such implementations, the central chamber inner space 22 may be defined between the portion of the proximal wall surface 212 bound between the peripheral chamber sidewalls 248 and the central chamber sidewalls 258, the peripheral chamber sidewalls 248, the peripheral chamber proximal wall 246, the central chamber sidewalls 258, the central chamber proximal wall 256, and the plurality of hollow extensions 226.

While the central inlet chamber 254 illustrated in FIG. 17 encompasses a plurality of hollow extensions 226, in alternative implementations, a central inlet chamber 254 may encompass a single hollow extension 226 (not shown).

While the central inlet chamber 254 illustrated in FIG. 17 encompasses the same hollow extensions 226 extending through the peripheral inlet chamber 244$^c$, in alternative embodiments, the central inlet chamber 254 may encompass a different amount of hollow extensions 226. For example, the central inlet chamber 254 may encompass only some (or even only one) of the hollow extensions 226 encompassed by the peripheral inlet chamber 244$^c$.

Preferably, the extension threading 232 of each of the hollow extensions 226, to which the caps 236 may be screwed, is positioned proximal to the central chamber proximal wall 256 to enable convenient attachment or release of the caps 236 to or from the hollow extensions 226, respectively.

In use, a first fluid stream may be directed through the peripheral chamber port 252$^c$ and the peripheral chamber opening 250$^c$ into the peripheral chamber inner space 20$^c$. Since the peripheral chamber inner space 20$^c$ is in fluid communication with the peripheral openings 218 surrounding a plurality of central bores 216, the fluid may further flow in a distal direction through the peripheral openings 218, for example into the membrane valve cavities 14, so as to deflect the respective plurality of membrane valve portions 150 to the peripheral open state, allowing the first fluid stream to flow onward into the internal cavity 12. Similarly, a second fluid stream may be directed through the central chamber port 262 and the central chamber opening 260 into the central chamber inner space 22. Since the central chamber inner space 22 is in fluid communication with the extension inlet openings 228 of the plurality of hollow extensions 226, into the gaps formed between the hollow extensions 226 and the respective tubes 50. The second fluid stream may further flow in a distal direction toward the central bores 216 and into the central gaps 16, so as to expand the distal ends 106 of the respective sealing valves 100 to the distal open state, flowing onward into the internal cavity 12.

Advantageously, each of the peripheral inlet chamber 244$^c$ and the central inlet chamber 254 illustrated in FIG. 17, encompassing a plurality of hollow extensions 226, enables a single stream of fluid, fed through a peripheral chamber opening 250$^c$ or a central chamber opening 260, respectively, to be directed toward more than one sealing valve 100, facilitating faster and more efficient process of directing such flows, for example during sterilization procedures.

Advantageously, separation between a peripheral inlet chamber 244 and a central inlet chamber 254 allows better control of the fluid flows through each flow path, for example if the timing or duration of fluid flow along the outer surfaces of the sealing member 100, as shown by arrows 40 in FIG. 5A, is different from that of the fluid flow along the inner surfaces, as shown by arrows 42 in FIG. 5B.

According to some exemplary implementations, a single peripheral inlet chamber 244 having a peripheral chamber proximal wall 246 proximal to the extension inlet openings 228, similar to the peripheral inlet chamber 244$^b$ described and illustrated in conjunction with FIG. 16, may encompass a plurality of hollow extensions 226, such as the plurality of hollow extensions 226 shown in FIG. 17 (exemplary implementations not shown). In such implementations, a single fluid stream may be directed concurrently directed through the extension inlet openings 228 of the plurality of hollow extensions 226, and through the peripheral openings 218 surrounding the plurality of central bores 216, so as to flow along both sides of the respective sealing valves 100 as described and illustrated in conjunction with FIG. 5C.

Reference is now made to FIG. 18, showing an exemplary configuration of sealing valves 100 mounted within opposing container walls 210, devoid of hollow extensions 226. As shows, in some configurations, two sealing valves 100a and 100b may be mounted within two opposite container walls 210, against central bores 216 which are coaxially aligned with each other. A single tube 50 may extend through both of the sealing valves 100a and 100b, such that it may be retained along two regions of its length by the distal ends 106a and 106b, and potentially by the distal segments 112a and 112b, respectively.

As shown in FIG. 18, when fluid flows through the one of central gaps 16, such as the central gap 16b, transitioning the sealing valve 100b to the distal open state, the opposite sealing valve 100a remains in a distal sealed state, irrespective of whether any of the membrane valve portions 150a or 150b are in the peripheral sealed state or the peripheral open state. Advantageously, this configuration allows transitioning of one sealing valve 100b to the distal open state, while the axial position of the tube 50 is retained by the opposite sealing valve 100a retained in the distal sealed state, without requiring additional hollow extensions 226 for keeping the tube 50 from slipping axially in such cases. This may reduce production costs and simplify attachment procedures.

Is some exemplary implementations, the container walls 210 of the configuration shown in FIG. 18, may further comprise a peripheral inlet chamber 244 surrounding a plurality of central bores 216, similar to the peripheral inlet chamber 244$^c$ shown in FIG. 17, but without any hollow extensions 226 extending there-through (exemplary implementations not shown). In such implementation, due to the absence of hollow extensions 226, a stream of fluid, flowing through the peripheral chamber opening 250, may propagate simultaneously through the plurality of central gaps 16, and through the peripheral openings 218 surrounding the plurality of corresponding central bores 216, so as to flow along both sides of the respective sealing valves 100 in a peripheral open state and a distal open state, as illustrated for the sealing valve 100b of FIG. 18.

Reference is now made to FIGS. 19-24B, showing different exemplary implementations of sealing valve 100 provided with side openings 126. FIG. 19 shows a view in perspective of a sealing valve 100 with side openings 126, according to some implementations. FIG. 20 shows a sealing assembly 200 with the sealing valve 100 of FIG. 19 in a peripheral sealed state and a distal sealed state thereof. FIG. 21 shows a sealing valve 200 which includes a container wall 210 devoid of peripheral openings 218, and the sealing valve 100 of FIG. 19 in a peripheral open state and a distal open state thereof. FIG. 22A shows a perspective view of a sealing valve 100 with side openings 126 and a proximal seal 124, according to some implementations. FIG. 22B shows a sectional view in perspective of the sealing valve 100 of FIG. 22A. FIG. 23 shows a sealing assembly 200 with the sealing valve 100 of FIGS. 22A-22B. FIG. 24A shows a cross-sectional view of the sealing assembly 200 of FIG. 23, in a peripheral sealed state and a distal sealed state of the sealing valve 100. FIG. 24B shows the sealing valve 200 of FIG. 24A, in a peripheral open state and a distal open state of the sealing valve 100.

According to some exemplary implementations, the main tubular body 102 further comprises at least one side opening 126 proximal to the membrane juncture 154. The at least one side opening 126 can include a plurality of side openings 126 circumferentially disposed around the main body 102, which may be equally or non-equally spaced from each other, such as the equi-spaced side openings 126 illustrated in FIG. 19-20. In some implementations, the side openings 126 are comprised in the proximal segment 108.

The at least one side opening 218 provides fluid communication between the central gap 16 and the membrane valve cavity 14. As shown in FIG. 20, the side openings 218 are spaced distally to the proximal end 104, so as to remain unblocked by the container wall 210 once mounted therein.

In the configuration illustrated in FIG. 20, fluid flowing through the central bore 216 toward the central gap 16, may propagate through the at least one side opening 126 toward the membrane valve cavity 14. Similarly, fluid flowing through the peripheral openings 218 into the membrane valve cavity 14, may propagate through the at least one side opening 126 toward the central gap 16. In both cases, the flowing fluid may transition the sealing valve 100 to the peripheral open state and the distal open state simultaneously. However, the configuration shown in FIG. 20 may result in a portion of the fluid flowing from the central gap 16 toward the membrane valve cavity 14, escaping through the peripheral openings 218, or a portion of the fluid flowing from the membrane valve cavity 14 toward the central gap 16, escaping to through the proximal end 104.

According to some implementations, the sealing valve 100 described and illustrated in conjunction with FIG. 19 is mounted within a container wall $210^a$, which may be identical to the container wall 210 according to any of the implementations described herein above, except that the container wall 210a is devoid of peripheral openings 218, as shown in FIG. 21. Thus, fluid flowing through the proximal end 104 in the direction of arrows 44, may propagate distally along the inner surface of the main body 102 so as to expand the distal end 106 to the distal open state, and simultaneously propagate through the at least one side opening 126 radially outward, so as to deflect the membrane valve portion 150 to the peripheral open state.

According to some implementations, a sealing valve 100 provided with at least one side opening 126 further comprises a proximal seal 124, extending radially inward from the proximal segment 108. The proximal seal 124 may extend from the proximal end 104, and may be formed as a unitary component continuous with the proximal flange 122, as shown in FIGS. 22A-22B. In alternative implementations, the proximal seal 124 may extends radially inward from any other portion of the proximal segment 108, that can be distal to the proximal end 104, as long as it is proximal to the at least one side opening 126 (alternative implementations not shown).

The inner diameter of the proximal seal 124 is chosen to match that of the outer diameter of the tube 50, so as to seal against the tube 50 when the tube 50 extends through the sealing valve 100, as shown in FIGS. 23-24B. In some implementations, the inner diameter of the proximal seal 124 is substantially equal to the outer diameter of the tube 50. In some implementations, the inner diameter of the proximal seal 124 is smaller than that of the outer diameter of the tube 50.

As shown in FIG. 24A, the proximal seal 124 blocks fluid passage through the proximal end 124 when the tube 50 extends there-through, such that the tube 50 may be retained by both the proximal seal 124 and the distal end 106 or distal segment 112 in the distal sealed state.

As shown in FIG. 24B, fluid flowing through the peripheral opening 218 in the direction of arrows 46, may deflect the membrane valve portion 150 to the peripheral open state, and simultaneously propagate through the at least one side opening 126 radially inward, into the central gap 16. Since the proximal seal 124 prevent fluid from exiting in the proximal direction, the fluid is directed therefrom in a distal direction so as to expand the distal end 106 to the distal open state.

Advantageously, the proposed configuration enabled the tube 50 to retain its axial position even in the distal open state, due to the proximal seal 124 remaining tightly pressed there-against, without requiring additional hollow extensions 226 for keeping the tube 50 from slipping axially in such cases. This may reduce production costs of the container wall 210 and simplify attachment procedures.

Reference is now made to FIGS. 25-26B, showing additional implementations for a sealing valve 100. FIG. 25 shows a cross-sectional view of a sealing valve 100 provided with a membrane valve portion $150^b$ having a flat surface section 158, according to some implementations. FIG. 26A shows a cross-sectional view of a sealing assembly 200, including the sealing valve 100 of FIG. 25 in a peripheral sealed state and a distal sealed state. FIG. 26B shows a cross-sectional view of the sealing assembly 200 of FIG. 26B, in a peripheral open state and a distal open state of the sealing valve 100.

In some exemplary implementations, the sealing valve 100 comprises a membrane valve portion $150^b$, which is similar to any of the implementations described for membrane valve portion 150 herein above, except that instead of being arched in a membrane-like configuration, the membrane body $152^b$ comprises a proximal flat surface section 158, configured to press in a relatively flat manner against the distal wall surface 214, thereby blocking the peripheral openings 218 in the peripheral sealed state without forming a membrane valve cavity 14.

In some exemplary implementations, as illustrated in FIG. 25, the membrane valve portion $150^b$ further comprises a depressed surface section 160, which is depressed distally relative to the flat surface section 158, bound between the proximal flat surface section 158 and the membrane juncture $154^b$. When mounted within the container wall 210, the depressed surface section 160 forms a narrow channel between the membrane juncture $154^b$ and the distal wall surface 214, as shown in FIG. 26A. This may be advantageous in facilitating flexure of the membrane body $152^b$ in a distal direction in the peripheral open state. In alternative implementations, the flat surface section 158 may extend all the way from the membrane lip $156^b$ to the membrane juncture $154^b$ (alternative implementations not shown).

As shown in FIG. 26A, the membrane body $152^b$ is biased in a proximal direction, so as to press the flat surface section 158 against the peripheral openings 218 in the peripheral sealed state. As further shown in FIG. 26B, fluid flowing through the peripheral openings 218 may directly hit the flat surface section 158 in a force sufficient to deflect the membrane body $152^b$ to the peripheral open state, wherein the axis of deflection can be either along the membrane juncture $154^b$, along the depressed surface section 160, or along a circumferential pivot line of the membrane body $152^b$ at a positioned between the membrane juncture $154^b$ and the peripheral openings 218.

According to some embodiments, there is provided a container sealing assembly 200, comprising a container wall 210 according to any of the implementations disclosed herein above, and at least one sealing valve 100, according to any of the implementations disclosed herein above, mounted therein. According to some embodiments, the container sealing assembly 200 further comprises at least one tube 50, extending through the at least one sealing valve 100.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although the invention is described in conjunction with specific embodiments thereof, it is evident that numerous alternatives, modifications and variations that are apparent to those skilled in the art may exist. It is to be understood that the invention is not necessarily limited in its application to the details of construction and the arrangement of the components and/or methods set forth herein. Other embodiments may be practiced, and an embodiment may be carried out in various ways. Accordingly, the invention embraces all such alternatives, modifications and variations that fall within the scope of the appended claims.

The invention claimed is:

1. A sealing valve, comprising:
   a main tubular body extending longitudinally between a proximal end and
   a distal end, comprising:
      a proximal segment extending distally from the proximal end; and
      a tapering segment extending from the proximal segment and tapering radially inward in the distal direction;
   a membrane valve portion extending around and radially away from the main tubular body, comprising:
      a membrane juncture, along which the membrane valve portion is attached to the main tubular body;
      a membrane body, extending radially away from the membrane juncture; and
      a membrane lip:
   wherein the membrane valve portion is resiliently biased toward the proximal direction, and is configured such that the membrane valve portion bends distally when flow-induced pressure gradient is applied thereto by fluid flowing in the distal direction;
   wherein the distal end is configured such that the distal end transitions between a distal free state, when no tube extends there-through, and a distal sealed state, when a tube extends there-through, sealing against the tube while no flow-induced pressure gradient is applied thereto; and
   wherein the distal end is made of a resilient flexible material, configured such that the distal end expands in the radial direction away from the tube extending there-through, when fluid pressure is applied to the distal end by distally-oriented fluid flow through the main body.

2. A sealing assembly, comprising at least one sealing valve according to claim 1, and:
   a container wall comprising:
      a proximal wall surface;
      a distal wall surface; and
      at least one central bore, and
   wherein the at least one sealing valve is mounted within the at least one central bore, such that the main tubular body extends through the at least one central bore.

3. The sealing assembly of claim 2, wherein the container wall further comprises at least one hollow extension, extending proximally from the peripheral wall surface around the central bore.

4. The sealing assembly of claim 3, wherein the at least one hollow extension comprises an extension inlet opening.

5. The sealing assembly of claim 4, further comprising a peripheral inlet chamber, comprising:
   at least one peripheral sidewall extending proximally from the proximal wall surface;
   a peripheral chamber proximal wall extending between the at least one peripheral chamber sidewall and the at least one hollow extension; and
   a peripheral chamber opening;
   wherein the at least one peripheral sidewall is disposed radially away from the at least one peripheral chamber opening.

6. The sealing assembly of claim 5, wherein the peripheral chamber proximal wall is distal to the extension inlet opening of the at least one hollow extension.

7. The sealing assembly of claim 6, further comprising a central inlet chamber, comprising:
   at least one central chamber sidewall extending proximally from the proximal wall surface or from the peripheral chamber proximal wall;
   a central chamber proximal wall extending between the at least one central chamber sidewall and the at least one hollow extension; and
   a central chamber opening;
   wherein the central chamber proximal wall is proximal to the extension inlet opening of the at least one hollow extension.

8. The sealing assembly of claim 2, wherein the container wall is a top cover of a container.

9. The sealing assembly of claim 2, wherein the container wall further comprises at least one peripheral opening offset radially outward from the at least one central bore.

10. The sealing assembly of claim 2, further comprising the tube extending axially through the main body.

11. The sealing assembly of claim 2, wherein the distal wall surface comprises a receiving channel accommodating the membrane lip.

12. The sealing assembly of claim 2, wherein the central bore comprises a bore groove spaced away from both the proximal wall surface and the distal wall surface, and such that the bore groove accommodates a proximal flange extending radially outward from the proximal segment of the sealing valve.

13. The sealing assembly of claim 2, wherein the central bore comprises a bore recess spaced away from the distal wall surface and open ended along the proximal wall surface, wherein the central bore accommodates a proximal flange extending radially outward from the proximal segment of the sealing valve.

14. The sealing valve of claim 1, further comprising a distal segment extending between the tapering segment and the distal end, wherein the distal segment is configured such that the distal segment transitions between the distal free state and the distal sealed state, while no flow-induced pressure gradient is applied thereto, and wherein the distal segment is made of a resilient flexible material, configured such that the distal segment expands in the radial direction when fluid pressure is applied to the distal end by distally-oriented fluid flow.

15. The sealing valve of claim 14, wherein the distal segment comprises a plurality of flaps, resiliently biased radially inward.

16. The sealing valve of claim 1, wherein the main tubular body further comprises at least one side opening proximal to the membrane juncture.

17. The sealing valve of claim 16, further comprising a proximal seal extending radially inward from the proximal segment.

18. The sealing valve of claim 1, further comprising a proximal flange extending radially outward from the proximal segment.

19. The sealing valve of claim 1, wherein the membrane body is arched from the membrane juncture in the proximal direction.

20. The sealing valve of claim 1, wherein the membrane body comprises a proximal flat surface section.

* * * * *